(12) United States Patent
Kawano et al.

(10) Patent No.: US 9,265,777 B2
(45) Date of Patent: *Feb. 23, 2016

(54) ANTIPARASITIC AGENT FOR FISH AND METHOD OF CONTROLLING PROLIFERATION OF FISH PARASITES

(75) Inventors: Fumi Kawano, Saiki (JP); Noritaka Hirazawa, Hachioji (JP)

(73) Assignee: NIPPON SUISAN KAISHA, LTD. (JP)

( * ) Notice: Subject to any disclaimer, the term of this patent is extended or adjusted under 35 U.S.C. 154(b) by 385 days.

This patent is subject to a terminal disclaimer.

(21) Appl. No.: 13/258,814

(22) PCT Filed: Apr. 26, 2010

(86) PCT No.: PCT/JP2010/057330
§ 371 (c)(1),
(2), (4) Date: Sep. 22, 2011

(87) PCT Pub. No.: WO2010/125991
PCT Pub. Date: Nov. 4, 2010

(65) Prior Publication Data
US 2012/0035181 A1    Feb. 9, 2012

(30) Foreign Application Priority Data
Apr. 27, 2009 (JP) .................. 2009-107390

(51) Int. Cl.
| | |
|---|---|
| A61P 33/02 | (2006.01) |
| A61K 31/433 | (2006.01) |
| A61K 31/42 | (2006.01) |
| A61K 31/635 | (2006.01) |
| A61K 31/505 | (2006.01) |
| A61K 31/519 | (2006.01) |
| A61K 45/06 | (2006.01) |

(52) U.S. Cl.
CPC .............. *A61K 31/635* (2013.01); *A61K 31/42* (2013.01); *A61K 31/433* (2013.01); *A61K 31/505* (2013.01); *A61K 31/519* (2013.01); *A61K 45/06* (2013.01)

(58) Field of Classification Search
USPC ........................................................ 514/249
See application file for complete search history.

(56) References Cited

U.S. PATENT DOCUMENTS

| | | | | |
|---|---|---|---|---|
| 3,461,206 A | * | 8/1969 | Hoffer et al. ................. | 514/157 |
| 2002/0037921 A1 | * | 3/2002 | Blair ............................ | 514/454 |
| 2010/0311759 A1 | | 12/2010 | Kawano et al. | |

FOREIGN PATENT DOCUMENTS

| | | |
|---|---|---|
| CN | 1386507 A | 12/2002 |
| JP | 49-13315 A | 2/1974 |
| JP | 51-16346 | 5/1976 |
| WO | 2009/057653 A1 | 5/2009 |
| WO | 2009063044 A1 | 5/2009 |

OTHER PUBLICATIONS

Weiss et al. (J. Agric. Food Chem., vol. 35, pp. 905-909; 1987).*
Robinson et al. (Journal of Aquatic Animal Health, vol. 2, Issue 1, abstract; 1990).*
Drugs.com (Retrieved on Mar. 22, 2013 from the Internet: <URL: http://www.drugs.com/vet/romet-30.html).*
Walisser et al. (J Chromatogr, vol. 518, No. 1, abstract; Sep. 28, 1990).*
Xu et al., Effect of cooking on residues of ormetoprim and sulfadimethoxine in the muscle of channel catfish, Food Research International, vol. 29, Nos. 3-4, pp. 339-344, 1996.*
Maki, Systemic and Cutaneous Mucus Antibody Responses of Channel Catfish Immunized against the Protozoan Parasite *Ichthyophthirius multifiliis*, Clin. Diagn. Lab. IMMUNOL, p. 876-881, 2003.*
Veterinary Pharmaceuticals and Devices, 1991, pp. 186-195 with partial English translation.
Dickerson, H. W., Dawe, D. L. (1995) *Ichthyophthirius multifiliis* and *Cryptocaryon irritans* (Phylum Ciliophora). In: Woo, P. T. K. (Ed), Fish Diseases and Disorders. Protozoan and Metazoan Infection, vol. 1, CAB International, UK, pp. 181-227.
International Search Report for International Application No. PCT/JP2010/057330 mailed Jun. 8, 2010 with English Translation.
Jin Shan, "Preliminary Studies on Pathogen and Hemopathology of the white cloud disease in Micropterus Salmoides", Acta Hydrobiologica Sinica, vol. 29, No. 2, 2005, pp. 184-188. (with Partial English translation).
Partial English Translation for Japanese Patent Application 51-16346, filed May 24, 1976.
Extended European Search Report for Application No./Patent No. 10769689.0-1216/2425857, dated Aug. 23, 2012, with English translation.

(Continued)

*Primary Examiner* — Jeffrey S Lundgren
*Assistant Examiner* — Zenab Olabowale
(74) *Attorney, Agent, or Firm* — Cantor Colburn LLP

(57) ABSTRACT

A method of controlling proliferation of fish parasites comprising the administration of 1 to 50 mg/kg fish body weight/day of an inhibitor of folate synthesis and/or an inhibitor of folate activation to fish continuously for 1 to 2 weeks. Using a combination preparation composed of an inhibitor of folate synthesis and an inhibitor of folate activation is preferable, and a sulfonamide is preferable for the inhibitor of folate synthesis. A dihydrofolate reductase inhibitor, a folate antagonist, etc., can be used as the inhibitor of folate activation. The antiparasitic agent is able to exterminate fish parasites via oral administration. It is particularly effective against parasites belonging to the ciliate group among fish parasites.

9 Claims, 12 Drawing Sheets

(56) References Cited

OTHER PUBLICATIONS

Ohno, et al. "The effect of oral antibiotic treatment and freshwater bath treatment on susceptability to *Neobenedenia girellae* (Monogenea) infection of amberjack (*Seriola dumerili*) and yellowtail (*S. quinqueradiata*) hosts", Aquaculture 292 (2009), pp. 248-251.

T. Wahli et al., "Evaluation of alternatives to malachite green oxalate as a therapeutant for ichthyophthiriosis in rainbow trout *Oncorhynchus mykiss*", J. Appl. Ichthyol. 9 (1993), pp. 237-249.

Amend, et al., "A Comparison of Oregon Pellet and Fish Meat Diets for Administration of Sulfamethazine to Chinook Salmon", Research Briefs, Fish Commission Oregon, 13, 20-24, 1967.

Amend, Donald F., et al., "The Administration of Sulfonamide Drugs to Adult Salmon", Prog. Fish-Cult., 30, 1968, pp. 168-172.

Donald F. Amend, et al., "Production Trials Utilizing Sulfonamid Drugs for the Control of "Cold Water" Disease in Juvenile Coho Salmon", Res. Briefs, Fish Comm Oregon, 11(1)14-17, 1965.

Amlacher, Erwin, "Textbook of Fish Diseases", TFH Publications, Jersey City, NJ, 1970.

Roger L. Herman, "Diseases of Fish", Symposia of the Zoological Society London, No. 30, 1972, pp. 141-151.

Herwig et al., "Handbook of Drugs and Chemicals Used in the Treatment of Fish Diseases", Published by Charles C. Thomas, Springfield, Illinois, 1979, pp. 66, 128-129, 197-199.

Hoffman, Glenn L. et al., "Parasites of Freshwater Fishes". TFH Publications, Ltd., Neptune City, New Jersey, 1974.

Postema, J.L., et al., "Ichthyophthiriose", EurekaMag.com Science Magazine, 81 (1), 1956, pp. 519-524.

Willford, Wayne A., "Toxicity of 22 Therapeutic Compounds to Six Fish", Fish Control, Laboratory, Wisconsin, No. 18, 1967, pp. 1-10.

E.M. Wood et al., "Sulfonamide Toxicity in Brook Trout", Trans Am Fish Soc, 84, 1957, pp. 155-160.

Kanai, Kinya, "Therapeutic Effect of a Combination of Sulfamonomethoxine and Ormetoprim against Edwardsiellosis in Japanese Flounder *Paralichthys olivaceus*," Bulletin of the Faculty of Fisheries of Nagasaki University, 2002, No. 83, 4 pp., with partial English Summary.

Sarashina et al., "Effects of Sulfamonomethoxine Combined with Ormetoprim on Bovine Coccidiosis," Journal of Japan Veterinary Association, 1998, vol. 51, No. 10, pp. 579-582, with partial English Summary.

Office Action for Japanese Application No. 2011-511384, dated Feb. 17, 2014 with partial English translation.

Notification of Reason for Rejection for Japanese Application No. 2009-539094; Date of Mailing: Jul. 18, 2013; 9 pgs., with English Translation.

"Antiprotozoals effective in vitro against the scuticociliate fish pathogen *Philasterides dicentrarchi*"; Authors: R. Iglesias et al.; vol. 49; pp. 191-197; 2002; Diseases of Aquatic Organisms; 8 pgs.

"Attempts to Control Whirling Disease by Continuous Drug Feeding"; Authors: Robert E. L. Taylor; Journal of Wildlife Diseases; vol. 9, Oct. 1973; pp. 302-305; 5 pgs.

"Efficacy of various chemotherapeutic agents on the growth of *Spironucleaus vortens*, an intestinal parasite of the freshwater angelfish"; Authors: Somboon Sangmaneedet, et al.; vol. 38, pp. 47-52, 1999; 7 pgs.

Office Action for the U.S. Appl. No. 12/740,531, dated Jul. 10, 2014.

Xu, et al., Effect of cooking on residues of ormetoprim and sulfadimethoxine in the muscle of channel catfish, 1996, Food Research International, vol. 29, Nos. 3-4, pp. 339-344.

\* cited by examiner

FIG. 13

| Experimental plot<br>Number of<br>days elapsed after exposure | Control plot 1<br>0mg | Experimental plot 1<br>50mg | Experimental plot 2<br>100mg | Experimental plot 3<br>250mg | Experimental plot 4<br>500mg |
|---|---|---|---|---|---|
| Average number of parasites (n) in 4 fish in each plot on after 5 days of exposure | 0 | 40 | 157 | 140 | 184 |
| Average number of parasites (n) in 4 fish in each plot on after 9 days of exposure | ≥ 1000 | 0 | 0 | 0 | 0 |
| Average number of parasites (n) in 3 fish in each plot on after 18 days of exposure | – | ≥ 1000 | 74.3 | 4 | 1 |
| Average number of parasites (n) in 5 fish in the experimental plot2 22 days after the exposure | – | – | 1092 | – | – |
| Average number of parasites (n) 29 days after the exposure Experimental plots 3 and 4 ( 5 fish each) | – | – | – | > 1000 | > 1000 |

FIG. 14

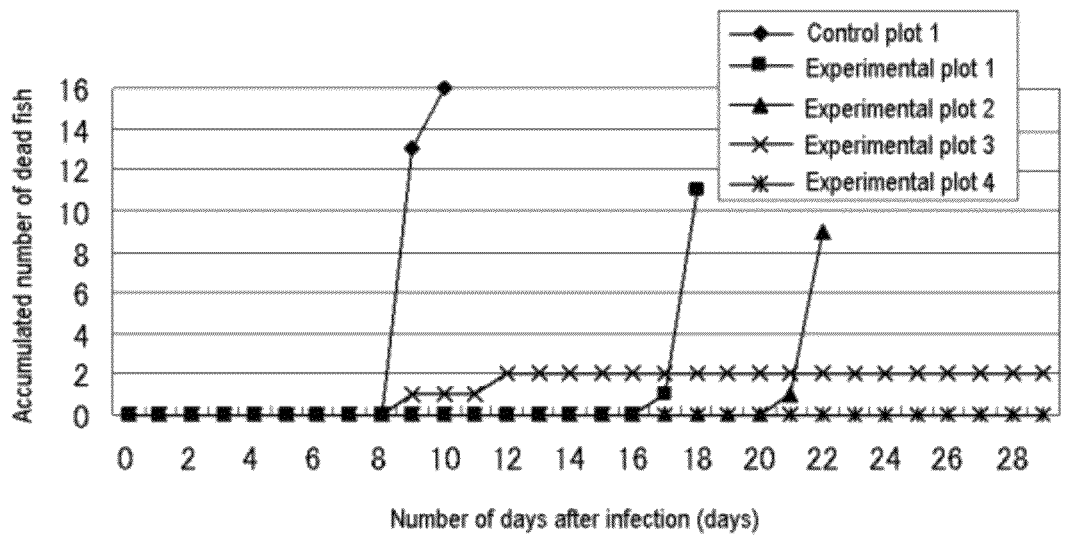

ANTIPARASITIC AGENT FOR FISH AND METHOD OF CONTROLLING PROLIFERATION OF FISH PARASITES

This is a U.S. national stage of application No. PCT/JP2010/057330, filed on Apr. 26, 2010. Priority under 35 U.S.C. §119(a) and 35 U.S.C. §365(b) is claimed from Japanese Application No. 2009-107390, filed Apr. 27, 2009, the disclosure of which is also incorporated herein by reference.

TECHNICAL FIELD

The present invention relates to a fish parasite expellant and a method of extermination. Specifically, it is a fish parasite expellant with an inhibitor of folate synthesis and/or an inhibitor of folate activation as the active substances. In particular, it relates to a fish parasite expellant and an extermination method in which parasitism is problematic for cultured fish.

BACKGROUND ART

Because parasitosis hinders stable production in mariculture, it is an extremely serious problem. *Cryptocaryon irritans*, which belong to the subkingdom Protozoa Phylum Ciliophora, parasitize sea fish and cause white spot disease. As a result, parasitized fish weaken to the point of death. In recent years, the parasitism of *Cryptocaryon irritans* on cultured fish has become a serious problem in the fish culture industry of Japan. *Cryptocaryon irritans* has thus far been reported as being parasitic to *Paralichthys olivaceus, Seriola dumerili, Seriola quinqueradiata, Pagrus major*, and *Takifugu rubripes. Cryptocaryon irritans* and *Ichthyophthirius rnultifiliis* are two types of ciliate protozoan that manifest as white spots on fish. The bionomics of *Cryptocaryon irritans* is similar to the bionomics of *Ichthyophthirius multifiliis*, which attracts white spot disease, wherein it repeats the stages of a trophont (imago) living in the body of a fish to which it is parasitic until the host dies, entirely leaving the fish to emerge as a protomont in the seawater, the protomont subsides and attaches to the sea bottom, where it ceases activity in a tomont (cyst, also known as a resistant egg), it is discharged again from the tomont, and it becomes a theront (larva) floating in the water in search of a fish that would become a host to which it can be parasitic. The trophont becomes parasitic on the epidermis and the branchial epithelial tissue of the fish and grows to a visible size, taking in nourishment from the body of the host.

The longevity of a theront is short and it can fairly readily be killed with a comparably weak drug. The phoront (parasitic larva) gains entrance to the epidermal layer near the dermis of the body surface of a fish and grow to an imago (trophont), so it is difficult to exterminate with drugs from the exterior of the body surface of these fish. A cyst is also covered by an outer shell, so it is difficult to exterminate it with drugs. Therefore, to exterminate the ciliate protozoa, it is necessary to periodically repeat a medicated bath in order to reduce the number of ciliate protozoa by exterminating the theront and trophont that have not infiltrated the dermal layer of the body surface and ultimately cut the multiplication cycle. Methods of extermination that take time in this way have been adopted, but there are cases in which it does not control damage to the extent of preventing the death of the fish.

As for orally administered medicine, lysozyme chloride has been authorized as fisheries medicine for combating White spot disease in *Pagrus major*. In addition, lactoferrin has also been marketed as an additive for fisheries (Patent Document 1). One report states that, when 40 mg of lactoferrin per 1 kg of fish body weight was orally administered per day during a 28-day experimental period, no infection was observed, as opposed to the majority of the fish dying after being given feed without any such additive. The mode of action of lysozyme chloride and lactoferrin is thought to be the increase in the non-specific biophylactic ability of the host fish, but the results are limited (Non-Patent Document 1). An antiparasitic agent that can directly exterminate parasites via oral administration is highly anticipated.

Sulfonamide is known as an antibacterial agent that has a sulfanilamide group, and the mechanism thereof is known to hinder the folate synthesis of bacteria. In addition, trimethoprim, ormetoprim, etc., are known as antagonists of folate metabolism, being drugs that demonstrate antibacterial action in the mechanism related to folic acid similar to that of sulfonamide. Methotrexate and aminopterin are derivatives of folic acid, which are variously used as anticancer agents and mouse poison.

In the category of antimicrobial/antibiotics, the combination preparations of sulfadimethoxine, sulfamonomethoxine, sulfamonomethoxine, and ormetoprim have been authorized as pharmaceutical products for fisheries. Sulfonamide was originally an antibacterial agent, but it is now known to be effective against malaria in humans, and against animal and avian coccidiosis, etc., as a pharmaceutical product for animals (Patent Document 2).

CITATION LIST

Patent Documents

Patent Document 1: Japanese Patent Application Publication No. H9-301807
Patent Document 2: Japanese Patent Publication No. S51-16346

Non Patent Documents

Non-Patent Document 1: Kazuo Ogawa (2004): Protozoal diseases. Infectious and parasitic diseases of fish and shellfish (eds. H. Wakabayashi, K. Muroga). Koseisha-Koseikaku. pp. 285-320.
Non-Patent Document 2: Dickerson, H. W., Dawe, D. L. (1995) *Ichthyophthirius multifiliis* and *Cryptocaryon irritans* (Phylum Ciliophora). In: Woo, P. T. K. (Ed), Fish Diseases and Disorders. Protozoan and Metazoan Infection, vol. 1, CAB International, UK, pp. 181-227.

SUMMARY OF INVENTION

Technical Problem

The present invention relates to an expellant of parasites in fish and particularly provides an expellant of ciliate protozoa. In particular, the goal of the present invention is to provide a method suitable for elimination of parasites in cultured fish cultured together in large numbers within the same environment such as an aquarium, fish preserve, or the like. Cultured fish are difficult to treat medically by isolation as separate individuals as would be done in the case of medical treatment of humans or animals, and when parasitosis occurs in even some of the fish within a aquarium or fish preserve, the infection quickly spreads to all the fish. Thus, even if an outbreak of parasitosis is confirmed in only some of the fish, medication must be administered to the entire aquarium or fish preserve in order to suppress all of the parasites. Moreover, if the parasites spread throughout a fishery, medication must be administered to all the fish preserves within the same fishery in order to suppress the parasites. Many fish preserves are located in oceans, lakes, and rivers and are open to the outside. Therefore, preventing parasites from entering such fish preserves is impossible.

Solution to Problem

The present inventors thoroughly studied a broad range of compounds to obtain a substance that would be effective as a antiparasitic agent for fish. They studied several substances that are known as antiparasitic drugs for animals, but parasites are also divided into various types themselves and there are diverse hosts, so it was not easy to find a substance that is effective against ciliate protozoa, because an antiparasitic drug that is effective in animals is not necessarily effective on parasitosis in fish. From among these, it was discovered that a substance having a mechanism related to folate metabolism was effective against ciliate protozoa, and the present invention was completed. A simultaneously pending patent application (PCT/JP2008/69673) relates to an anti-parasitic agent for fish including as an effective ingredient a inhibitor of folate synthesis and/or a inhibitor of folate activation. According to the present invention, a dosage or utilization method is provided for the elimination of parasites of cultured fish cultured together in large numbers in a culturing location, particularly a fish preserve or the like.

The present invention provides a antiparasitic agent with the following characteristics (1) to (10).

(1) A method of controlling proliferation of fish parasites, comprising the administration of 1-50 mg/kg fish body weight/day of an inhibitor of folate synthesis and/or an inhibitor of folate activation to fish.

(2) The method according to (1), comprising the administration of an inhibitor of folate synthesis and/or an inhibitor of folate activation continuously for 1 to 2 weeks.

(3) The method according to (1) or (2), comprising the administration of the inhibitor of folate synthesis and the inhibitor of folate activation as a combination of drugs.

(4) The method according to any one of (1) to (3), wherein the inhibitor of folate synthesis is a sulfonamide.

(5) The method according to (4), wherein the sulfonamide is any one of sulfamethoxazole, sulfamonomethoxine, sulfadimethoxine, sulfamerazine, sulfisoxazole, sulfisomidine, sulfamethizole, sulfisozole, or a pharmaceutically acceptable salt thereof.

(6) The method according to any one of (1) to (5), wherein the inhibitor of folate activation is a dihydrofolate reductase inhibitor.

(7) The method according to (6), wherein the inhibitor of folate activation is any one of pyrimethamine, trimethoprim, ormetoprim, methotrexate, denopterin, pteropterin, aminopterin, edatrexate, piritrexim, or a pharmaceutically acceptable salt thereof.

(8) The method according to any one of (1) to (7), wherein the parasite is a parasite belonging to the subkingdom Protozoa.

(9) The method according to (8), wherein the parasite is a parasite belonging to the subkingdom Protozoa Ciliophora.

(10) The method according to (9), wherein the parasite is *Cryptocaryon irritans* or *Ichthyophthirius multifiliis*.

(11) The method according to any one of (1) to (10), wherein the fish is a *Perciformes, Pleuronectiformes, Clupeiformes, Tetraodontiformes, Cypriniformes, Anguilliformes, Siluriformes, Rajiformes, Characiformes, Labroidei, Anabantoidei, Gobioidei, Cyprinodontiformes, Osteoglossiformes, Semionotiformes, Polypteriformes, Beloniformes, Atheriniformes,* or *Synbranchfformes* fish.

Advantageous Effects of Invention

The fish antiparasitic agent according to the present invention is able to exterminate fish parasites and particularly parasites belonging to the phylum Ciliophora. In particular, it is effective against ciliate protozoa that have become problematic in the fish culture industry. The ciliate protozoa expellant according to the present invention can be administered orally, particularly via a method of mixing with feed before feeding and demonstrates a growth inhibition effect and a pesticidal effect against parasites that are parasitic to the bodies of fish. The dosage/utilization method of the present invention is suitable for elimination of parasites of fish cultured together in large numbers in a culturing location. Specifically, as the parasite is being suppressed by a low dosage, the parasite is eradicated by 1 to 2 weeks of continuous administration of the drug. Therefore the burden imposed on the fish is slight, the occurrence of drug-resistant strains in the culturing location is suppressed, and residue from the drug is minimized. Moreover, continuously administrating the drug for 1 to 2 weeks sustains the effects upon the next generation of parasites, and can also control new parasites arriving from the aquatic environment. In short, parasite control is possible for an entire fish farm.

BRIEF DESCRIPTION OF DRAWINGS

In FIG. 3, * means P<0.01.

In FIG. 4, the leftmost bar shows control plot in which no drug administered. The second to eighth bars show respectively the result of the plot in which any one of folate synthesis inhibitors (SDMX, SMXZ, SMMX, SMDN, SID, SMZ, or SIZ) was administered 300 mg/kg fish body weight/day for three days. The ninth to twelfth bars show respectively the result of the plot in which any one of folate activation inhibitors (MTX, PRY, TMP, or PMD) was administered 60 mg/kg fish body weight/day for three days. The rightmost bar shows the result of the plot in which folate synthesis inhibitor (SDMX+TMP) was administered 216 mg SDMX/kg fish body weight/day and 24 mg TMP/kg fish body weight/day. There were the statistically significant difference between control plot and each other plots (P=<0.01).

FIG. 6 (*b*) is a figure showing a comparison of the number of parasites 5 days after the exposure in each plot in Example 5.

FIG. 7 (*a*) shows the number of cysts 5 days and 9 days after the exposure in each plot. White bars show the result of 5 days after the exposure and black bars show that of 9 days after the exposure. FIG. 7 (*b*) shows the size of the cysts 5 days after the exposure. In (a) and (b), * means $P<0.01$.

FIG. 9 (*b*) is a figure showing the size of the cysts five days after the exposure in each plot in Example 6. In (a) and (b), * means $P<0.01$.

FIG. 12 (*b*) is a figure showing the mean body length of the parasites five days after the exposure in each plot in Example 7. In (b), * means $P<0.05$.

FIG. 13 is a table showing the change in number of parasites after the exposure in each plot in Example 7.

FIG. 14 is a figure showing a comparison of the number of dead fish in each plot in Example 7.

FIG. 15 (*b*) is a figure showing a comparison of the mean body lengths of the ciliate protozoan parasites that were parasites to *Takifugu rubripes* three days after the exposure in each plot in Example 8. In (b), * means $P<0.01$.

FIG. 16 (*b*) is a figure showing a comparison of the mean body lengths of the ciliate protozoan parasites that were parasites on *Paralichthys olivaceus* three days after the exposure in each plot in Example 9. In (a), * means $P<0.05$ and ** means $P<0.01$. In (b), * means $P<0.01$.

FIG. 17 (*b*) is a figure showing a comparison of the mean body lengths of the ciliate protozoa parasites that were parasitic to *Seriola dumerili* three days after the exposure in each plot in Example 10. In (a), * means $P<0.05$. In (b), * means $P<0.01$.

FIG. 18 (*b*) is a figure showing a comparison of the mean body lengths of the ciliate protozoan parasites that were parasitic to *Epinephelus septemfasciatus* three days after the exposure in each plot in Example 11. In (a), * means $P<0.05$. In (b), * means $P<0.05$ and ** means $P<0.01$.

DESCRIPTION OF EMBODIMENTS

Figure 1:
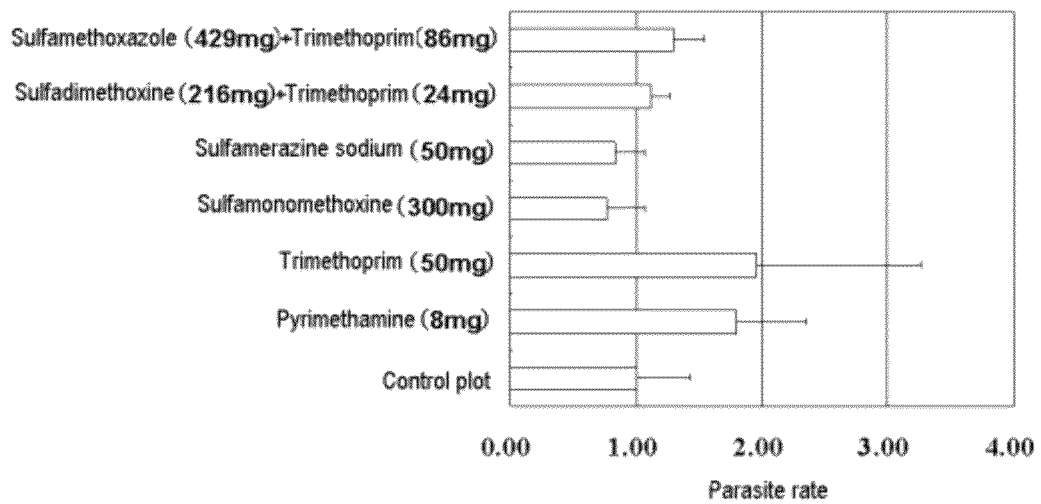
FIG. 1 is a figure showing the results of Example 1 by number of parasites in each plot when the number of parasites on the control plot is one.

The fish in the present invention include both marine fish and fresh water fish among the fish species. In practical use, these fish species were handled as cultured fish and aquarium fish, due to which the need arose to exterminate parasites thereon. Therein, what is most important, particularly to industry, is cultured fish, and for example, it is possible to use the methods of the present invention prophylactically or therapeutically in fish species in which the parasitism of fish parasites such as ciliate protozoa is known, such as *Tetraodontiformes Tetradontidae Takifugu rubripes, Perciformes Serranidae, Perciformes Cichlidae Oreochromis, Siluriformes Cypriniformes Siluridae* such as *Silurus asotus, Cypriniformes Ctenopharyngodoninae Ctenopharyngodon idellus* (Grass Carp), *Abramidinae Hypophthalmichthys molitrix* (Silver carp), or *Aristichthys nobilis* (Bighead carp), *Salmoniformes Salmonidae Salmo salar* (Atlantic salmon), *Oncorhynchus tshawytscha* (Chinook salmon), or *Oncorhynchus mykiss* (Rainbow trout), *Siluriformes Ictaluridae Ictalurus punctatus* (Channel catfish), *Pangasiidae Tra* or *Basa, Cypriniformes Cyprininae* Goldfish or Koi or in fish species in which there is a possibility of the parasitism of fish parasites.

The fish species that are the subject of the present invention include all ages of cultured fish as well as aquarium and commercial ornamental fish that are living in freshwater and seawater. Fish species in which the parasitism particularly of ciliate protozoa, etc., is known are cultured fish such as *Perciformes, Pleuronectiformes, Clupeiformes, Tetraodontiformes, Cypriniformes, Anguilliformes, Siluriformes, Gonorynchiformes, Rajiformes, Characiformes Labroidei, Anabantoidei, Gobioidei, Cyprinodontiformes, Osteoglossiformes, Semionotiformes, Polypteriformes, Beloniformes, Atheriniformes,* and *Synbranchiformes*, as well as fish such as *Perciformes Carangidae Seriola* (amberjack/yellowtails), *Perciformes Epinephelinae* (groupers), *Perciformes Sparidae* (breams), *Pleuronectiformes Paralichthyidae* (flounders), *Salmoniformes Salmonidae* (salmons), *Tetraodontiformes Tetraodontidae* (puffers), *Cypriniformes Cyprinidae* (carps), *Anguilliformes Anguillidae* (eels), *Siluriformes Pangasiidae, Siluriformes Ictaluridae* (catfishes), *Danioninae, Cobitidae, Puntius, Anabantidae,* Freshwater puffer fish, *Cichlidae, Siluriformes, Characiformes, Platy, Poecilia, Poecilia, Gourami, Betta,* Snakehead, Oviparous killifish, Goldfish, and *Carassius*. Specific examples are *Seriola dumerili*, Greater amberjack *Seriola dumerili, Seriola quinqueradiata, Seriola lalandi, Trachurus japonicus, Pseudocaranx dentex, Scomber japonicus, Lateolabrax japonicus, Pagrus major, Oplegnathus fasciatus, Oplegnathus punctatus, Oreochromis*

*mossambicus, Rachycentron Canadum, Epinephelus akaara, Epinephelus bruneus, Epinephelus septemfasciatus, Epinephelus malabaricus, Cromileptes altivelis, Plectropomus leopardus, Epinephelus lanceolatus, Epinephelus coioides, Sebastiscus marmoratus, Thunnus thynnus*), *Thunnus maccoyii, Thunnus obesus, Thunnus albacares, Thunnus alalunga, Paralichthys olivaceus, Verasper moseri, Verasper variegatus, Psetta maxima, Hippoglossus, Oncorhynchus mykiss, Salmo salar, Oncorhynchus kisutch, Oncorhynchus nerka, Plecoglossus altivelis altivelis, Takifugu rubripes, Stephanolepis cirrhifer, Zebrasoma flavescens, Cyprinus carpio carpio, Anguilla japonica, Anguilla anguilla, ktalurus punctatus, Chanos chanos* (Milkfish), Silver carp, Bighead carp, Grass Carp, *Siniperca chuatsi, Nile Tilapia, Odontesthes bonariensis, Lates calcarifer*, European perch, Red Drum, Common Carp, *Cobia, Basa, Tra, Catla, Roho labeo, Trigonostigma heteromorpha, Trigonostigma hengeri, Trigonostigma espei, Sundadanio axelrodi, Boraras maculatus, Acantopsis choirorhynchos, Pangio kuhlii, Chromobotia macracanthus, Puntius tetrazona* var., *Puntius ticto, Danio albolineatus, Poecilia velifera, Poecilia sphenops, Tanichthys albonubes, Tanichthys micagemmae, gourami, Betta, Snakehead, Tetraodon nigroviridis, Tetraodon biocellatus, Tetraodon palembangensis, Tetraodon turgidus, Dasyatis, Xenetodon cancila, Dermogenys pusillus, Periophthalmus modestus, Osteoglossum bicirrhosum, Osteoglossum ferreirai, Scleropages formosus, Scleropages jardini, Scleropages leichardti, Astronotus ocellatus, Astronotus orbiculatus, Pterophyllum, Pterophyllum altum, Pterophyllum scalare, Symphysodon, Apistogramma, Papiliochromis ramirez, Papiliochromis altispinosa, Biotoecus opercularis, Apistogramma, Apistogrammoides pucallpaensis, Amphilophus citrinellus, Nannacara, Dicrossus, Corydoras, Liposarcus multiradiatus, Otocincrus, Paracheirodon axelrodi, Paracheirodon innesi, Paracheirodon axelrodi, Paracheirodon simulans, Hemigrammus bleheri, Hemigrammus erythrozonus, Hyphessobrycon herbertaxelrodi, Hyphessobrycon pulchripinnis, Moenkhausia pittieri, Hyphessobrycon sweglesi, Nematobrycon palmed, Thayeria boehlkei, Serrasalmus spilopleura, Pygocentrus nattereri, Serrasalmus rhombeus, Pygocentrus Piraya, Aphyosemion, Epiplatys, Nothobranchius, Procatopus, Aplocheilicthys, Aulonocara baenschi, Melanochromis auratus, Sciaenochromis Fryeri, Labidochromis caeruleus, Julidochromis transcriptus, Hemichromis bimaculatus, Tilapia buttikoferi, Neoceratodus forsteri, Melanotaenia praecox, Melanotaenia plaecox, Iriatherina werneri., Pseudomugil gertrudae, Pseudomugil furcatus, Telmatherina ladigesi, Bedotia geayi, Badis badis, Erpetoichthys calabaricus, Polypterus, Polypterus bichir bichir, Carassius auratus auratus*, Koi The parasites in the present invention are protozoa. According to the earlier taxonomy proposed in 1980 by the International Society of Protistologists, protozoa including species occurring in fish are classified as belonging to the phyla Sarcomastigophora, Ciliata, Apicomlexa, Microspora, or Myxozoa.

However, in recent years, this taxonomy has been radically revised. According to the latest taxonomy announced by the International Society of Protistologists in 2005, all eukaryotes are divided into six supertypes and distributed among subordinate primary and secondary subtypes. Moreover, this taxonomy differs greatly from the earlier taxonomy in that the previous categories of kingdom and phylum are not used in naming the supertypes, the previous Sarcomastigophora phylum has been divided among various super-groups, and so forth. This new taxonomy is based on molecular biological data and electron microscope observation, and this results in an advance from an artificial taxonomy to a more systematic one. Although it is thought that the fundamental thrust of this new system will be widely accepted, areas of unresolved problems still remain, and future revision is possible (Kazuyoshi Yoshinaga and Hiroshi Yokoyama, Fish Pathology Survey—Revised (edited by Kazuo Ogawa and Kiyokuni Muroga) Kouseisha-kouseikaku Corp., p. 92).

Among these, the present invention is effective on ciliates belonging particularly to ciliate protozoa. Specifically, examples include ciliate protozoa (*Ichthyophthirius multifiliis, Cryptocaryon irritans*), *Trichodina* (*Trichodina* sp.), *Chilodonella* (*Chilodonella* sp.), Kinetofragminophora *Brooklynella hostilis, Uronema* Infestations (*Uronema marinum, Philasterides dicentrarchi, Miamiensis avidus, Uronema nigricans, Uronema* sp.) belonging to ciliates. In particular, it is effective on *Cryptocaryon irritans* and *Ichthyophthirius multifiliis*.

The present inventors discovered that a drug having a mechanism that hinders the function of folic acid as an inhibitor of folate synthesis, an inhibitor of folate activation, etc., has the effect of exterminating fish parasites. Not only do these drugs exterminate parasites but they also hinder parasite growth. This shows that ciliate protozoa synthesize folic acid themselves and that folic acid is an essential component for the survival and growth of protozoa. When a combination preparation of an inhibitor of folate synthesis and an inhibitor of folate activation is administered, the inhibition of growth and the parasiticidal effect was observed more clearly. Very few of these parasites have become cysts, and comparing the size thereof to the control plot, it is notably small. As a result of observing these cysts for twelve days, a delay in hatching and the developmental anomaly of the cysts is evident, wherein they do not grow normally. Therefore, the drugs that have the effect of impeding the synthesis and use of folic acid are effective in exterminating the fish parasites.

The inhibitor of folate synthesis according to the present invention is a class of drugs that are known as antibacterial agents. Bacteria pass through several stages of reactions with guanosine as the raw material, biosynthesizing 2-amino-4-hydroxy-6-hydroxymethyl dihydropteridine pyrophosphate supplemented by paraminobenzoic acid (PABA) to become dihydropterin acid (DHP). DHP synthetase is the enzyme that catalyzes this reaction, and the inhibitor of folate synthesis represented by sulfonamide acts as a PABA antimetabolite, hindering the synthesis of DHP. As a result, bacteria become unable to biosynthesize folic acid. Tetrahydrofolic acid (THF) is a coenzyme that is essential in the biosynthesis of nucleobases such as purine and thymine or amino acids such as methionine, serine, and glycine, so the propagation of bacteria is suppressed when the synthesis thereof is hindered. On the other hand, higher animals such as humans are not subject to the effect of sulfonamides, because they do not have a DHP synthesis pathway and THF is synthesized by breaking down folic acid that has been taken in from external sources. Para-aminosalicylic acid, which is an antiphthisic drug, and diaminodiphenyl sulfone, which is an antileprosy drug, both show antibacterial activity with the same mechanism. Sulfonamide is a generic term for a class of compounds which has a sulfanilamide as a basic skeleton and the amide group is substituted by a variety of heterocycles. Several thousand of sulfonamides are synthesized, but the sulfonamides used in the present invention are those for which the safety and effects on humans and animals have been verified, and it is preferable to use sulfonamides that are utilized as antibacterial agents particularly for fish. Examples of these sulfonamides are sulfamethoxazole, sulfamonomethoxine, sulfadimethoxine, sulfamerazine, sulfisoxazole, sulfisomidine, sulfamethizole, sulfisozole, and still other sulfonamides include sulphadimidine (sulfamethazine), sulfaquinoxaline, sulfadiazine (sulfadiazine), sulfaguanidine, sulfacetamide, sulfamethoxypyridazine, sulfaethoxypyridazine, sulfachlorpyrazine, sulfachlorpyridazine, sulfasalazine, sulfatroxazole, sulfathiazole, sulfabenzamide, sulphadoxine, sulfanitran, sulfanilamide, sulfapyridine, sulfabromomethazine, sulfamoildapsone, pralatrexate (next-generation folate antagonists), etc.

The inhibitors of folate activation according to the present invention are drugs that are referred to as inhibitors of folate activation, folate antagonists, folic acid analogs, etc., that are involved in the metabolism of folic acid other than inhibitors of folate synthesis. Dihydrofolate reductase inhibitor is known as the main inhibitor of folate activation. It is an inhibitor of enzymes in which dihydrofolate is reduced to the active form of tetrahydrofolic acid. These are used as a combination preparation with inhibitors of folate synthesis and have been known to show a synergistic effect as antibacterial agents. In addition, folate antagonists, also called folic acid analogs, are known as drugs which have a structure similar to folic acid and hinder the activation of folic acid via enzyme inhibition. Pyrimethamine, trimethoprim, ormetoprim, methotrexate, denopterin, pteropterin, aminopterin, edatrexate, piritrexim, diaveridine, pentamidine, pemetrexed, trimetrexate, etc., are known as these inhibitors of folate activation.

The antiparasitic agent according to the present invention can act through oral administration. In addition, administration via injection and administration via a medicated bath in which the fish are immersed in a liquid in which the drug has been dissolved are also possible.

The dosage of the antiparasitic agent according to the present invention, in the case of oral administration, is 1-2,000 mg/kg of the inhibitor of folate synthesis, the inhibitor of folate activation, or the aforementioned combination preparation of an inhibitor of folate synthesis and an inhibitor of folate activation per 1 kg of fish body weight per day, and preferably within the range of 1-1,000 mg/kg. Furthermore, one to fifteen days is appropriate for one treatment period. In the case of an aquarium, which is a closed system, it is also possible to completely eliminate parasites, but in a fish preserve that comes in contact with the open sea, the survival of parasites and the state of survival differs according to the environment, so it is preferable to alternate between discontinuation periods and the aforementioned treatment period while seeking to ascertain the health status of the fish and the parasitic state of the parasites. For example in case of using a combination preparation of sulfamonomethoxine and ormetoprim or that of ulfadimethoxine and pyrimethamine, a sufficient effect can be obtained with oral administration of these drags 25-500 mg per 1 kg of fish body weight per day for three to fifteen days. In consideration of the life cycle of the parasites, it is preferable to repeat this administration.

Separate culturing of parasite-infected fish is not possible when culturing a large number of fish together in an aquarium, fish preserve, or the like, unlike the case of raising a small number of ornamental fish or the like. As such, if even just some of the fish are found to be infected, drugs must be administered to all of the fish in the fish farm. In such instances, the ability to suppress the parasite using a minimal drug dosage and to minimize the total amount of the drug utilized is desirable. Since the drug of the present invention also has an anti-microbial effect, use of a large amount of the drug is undesirable as it can lead to the rise of drug-resistant strains of bacteria. The burden imposed on the fish also decreases as the utilized amount of the drug is decreased. Although the size of the dose administered will vary according to the degree that the parasitic infection has spread and the type of fish, the inhibitor of folate synthesis and/or the inhibitor of folate activation is preferably administered orally continuously for 1 to 2 weeks at a dosage of 1-50 mg/kg fish body weight/day, more preferably at a dosage of 5-25 mg/kg fish body weight per day. The next generation of the parasite can also be suppressed by continuous oral administration of these dosages for 1 to 2 weeks. The parasitic infection status of the fish is checked after administrating the drug or after continuous administration for about 1 to 2 weeks. In many cases, parasitic inventions of cultured fish can be controlled by administration of 5-25 mg/kg fish body weight per day continuously for 5 to 20 days, preferably for 1 to 2 weeks. If examination of the gills, etc. reveals that multiple fish are infected with a parasite, treatment via the same method of administration and dosage level is repeated. Even if no parasitic infection is discovered during examination, checks for parasite infection are preferably conducted periodically about every two weeks.

In addition, by dissolving the expellant in rearing water and thereby immersing the body of the fish therein, it is possible to induce direct contact therewith, and in that case, the active substance is dissolved in the rearing water to a concentration of 0.5-500 ppm, causing direct contact with the target fish for a period of 10 min. to 15 days. In the case of injection, administration would be 0.1-200 mg/kg per injection, and preferably 0.5-100 mg/kg. Furthermore, in such a case, one to fifteen days are appropriate for a treatment period.

The antiparasitic agent according to the present invention can be administered alone, or as needed, it can be used with other substances for example, in combination with an auxiliary component such as a carrier, a stabilizer, an excipient, or a diluent. Inhibitors of folate synthesis and inhibitors of folate activation are widely used for humans and animals, and various formulations are known in which compounds are used as antibacterial agents also for fish. These formulations that are used can also be used in the case of the purpose of the present invention.

In addition, forms that may be used for these compounds include powder, granules, tablets, capsules, etc., and any other conventional form. In the case of fish that are sensitive to the taste and odor of the compound, it is possible to create a compound that does not readily leak by applying a method such as coating to prevent the degradation of palatability.

In the case of fish, orally-administered drugs are usually used by being mixed with feed. When the antiparasitic agent according to the present invention is mixed with feed, it is preferable to use feed in which the nutritional components and physical properties that are necessary for each fish species are taken into consideration. Feed usually used are a pellet made by mixing fish meal, bran, starch, minerals, vitamins, fish oil, etc., and forming, and a pellet made by mixing frozen fish such as sardines and powder feed (mash) including supplements such as vitamins and forming. The species and size of the fish, decides the daily feed intake almost entirely, so the amount of this antiparasitic agent to be added to feed is calculated according to the aforementioned use and dosage. The daily dose of this parasite exterminator can be administered as one dosage or divided in several dosages.

Examples of the present invention are noted below, but the present invention is not limited to these in any way.

The drugs used in these Examples are the following preparations.

Sulfamonomethoxine+ormetoprim combination preparation (Sulfamonomethoxine, Ormetoprim)
Trade name: "Suisanyo Ekuteshin"; Manufacturer/Distributor: Meiji Seika Kaisha, Ltd.;

Maker: Daiichi Fine Chemical Co., Ltd.
  Sulfamonomethoxine (Sulfamonomethoxine)
Trade name: "Suisanyo Daimeton Soda"; Manufacturer/Distributor: Meiji Seika Kaisha, Ltd.;
Maker: Daiichi Fine Chemical Co., Ltd.
  Sulfisozole sodium (Sulfisozole Na)
Trade name: "Isuran Soda"; Distributor: Schering-Plough Animal Health;
Manufacturer/Distributor: SERACHEM Co., Ltd.
  Sulfamethoxazole (Sulfamethoxazole), sulfadimethoxine (Sulfadimethoxine), sulfisomidine, Reference standard (Sulfisomidine), pyrimethamine (Pyrimethamine), trimethoprim (Trimethoprim), methotrexate (Methotrexate), Wako Pure Chemical Industries, Ltd.; Reagent
  Ormetoprim Reference standard (Ormetoprim), Kanto Chemical Co., Inc.; Reagent
  Pentamidine isetionate salt (Pentamidine Isetionate Salt), sulfamerazine (Sulfamerazine), sulfamethizole (Sulfamethizole), SIGMA-ALDRICH Japan K.K.; Reagent
  When it is stated that the drug is added to pellets in the Examples, the drug is dissolved in an aqueous solution that includes a low glycated reduction syrup (Esui-30, Nikken Chemical and Synthetic Industry Co., Ltd.) and is spread on the surface of pellets to be used.

Example 1

Parasiticidal Effect of the Oral Administration of an Inhibitor of Folate Synthesis and an Inhibitor of Folate Activation on the Parasitism of *Cryptocaryon irritans* on *Pagrus major* (1)

Test method: Seventy *Pagrus major* with an average weight of 20 g were reared for approximately 7 days in a 200-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 200-liter aquarium was stopped and approximately 200,000 *Cryptocaryon irritans* hatched larva were put into the aquarium, then the fish were exposed to the parasites for 1 hour. After exposure, ten fish each were moved into seven 100-liter aquariums. During the rearing period, 1.2 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the number of *Cryptocaryon irritans* parasitizing the left gills were counted. Furthermore, the size of the parasites was observed at the same time.

Experimental plot: A plot in which 8 mg pyrimethamine/kg body weight/day was orally administered for three days, a plot in which 50 mg trimethoprim/kg body weight/day was orally administered for three days, a plot in which 300 mg sulfamonomethoxine/kg body weight/day was orally administered for three days, a plot in which 50 mg sulfamerazine sodium/kg body weight/day was orally administered for three days, a plot in which 216 mg sulfadimethoxine and 24 mg trimethoprim/kg body weight/day was orally administered for three days, a plot in which 429 mg sulfamethoxazole and 86 mg trimethoprim/kg body weight/day was orally administered for three days, and a control plot in which drug additive-free feed was fed were set up for a total of 7 plots. Test feeds were prepared by mixing a predetermined amount of each drug into moist feed (fish meal, fish oil, active gluten, guargum, vitamin mix, mineral mix, feed oil, and soy bean lecithin were proportionally mixed at 80, 3, 2, 4, 3, 6, and 2 wt %, respectively, and pellets were formed by thoroughly mixing 30 wt % of water into this powder).

Assessment of the effect: The number of parasites was compared, and the morphology of the parasites was observed.

As a result of having observed the parasite morphology, it was clear that the size of the parasites of every medication plot parasitizing the gills of the *Pagrus major* were smaller than those parasitizing the fish of the control plot. The body length of the parasites was approx. 350 µm in the control plot and 100-250 µm in all of the medication plots. These results show that an inhibitor of folate synthesis and an inhibitor of folate activation hinder the growth of these parasites in common. Thus, it has become clear that the parasites synthesize folic acid themselves, and the drug is able to suppress the growth of these parasites by hindering such synthesis. The resulting numbers of parasites are shown in FIG. 1. It shows the number of parasites in the pyrimethamine administration plot, the trimethoprim administration plot, the sulfadimethoxine and trimethoprim administration plot, and the sulfamethoxazole and trimethoprim administration plot tend to be large. This result is interpreted that because of the extreme hindering of the growth of these parasites, leaving from hosts in order to become cysts was delayed. In the life cycle of *Cryptocaryon irritans* in sea water with a temperature of about 25° C., larva that are approx. 30 µm in size first hatch from cysts within about four days, they become parasitic on the gills and body surface of a host fish, taking nourishment from the host for about three days, and grow to as much as 350 µm in size. These grown parasites then leave the host to become cysts.

Example 2

Parasiticidal Effect of the Oral Administration of an Inhibitor of Folate Synthesis and an Inhibitor of Folate Activation on the Parasitism of *Cryptocaryon irritans* on *Pagrus major* (2)

Test method: Twenty-four *Pagrus major* with an average weight of 39 g were reared for approximately 7 days in a 200-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 200-liter aquarium was stopped and approximately 170,000 *Cryptocaryon irritans* hatched larva were put into the aquarium, then the fish were exposed to the parasites for 1 hour. After exposure, eight fish each were moved into three 100-liter aquariums. During the rearing period, 1.2 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the body length of the *Cryptocaryon irritans* parasitizing the gills was measured.

Experimental plot: A plot in which 216 mg sulfadimethoxine and 24 mg trimethoprim/kg body weight/day was orally administered for three days, a plot in which 429 mg sulfamethoxazole and 86 mg trimethoprim/kg body weight/day was orally administered for three days, and a control plot in which no drug added feed was fed were set up. Test feeds were prepared by mixing a predetermined amount of each drug into moist feed.

Assessment of the effect: The body lengths of the parasites parasitizing the gills were compared.

Figure 2:
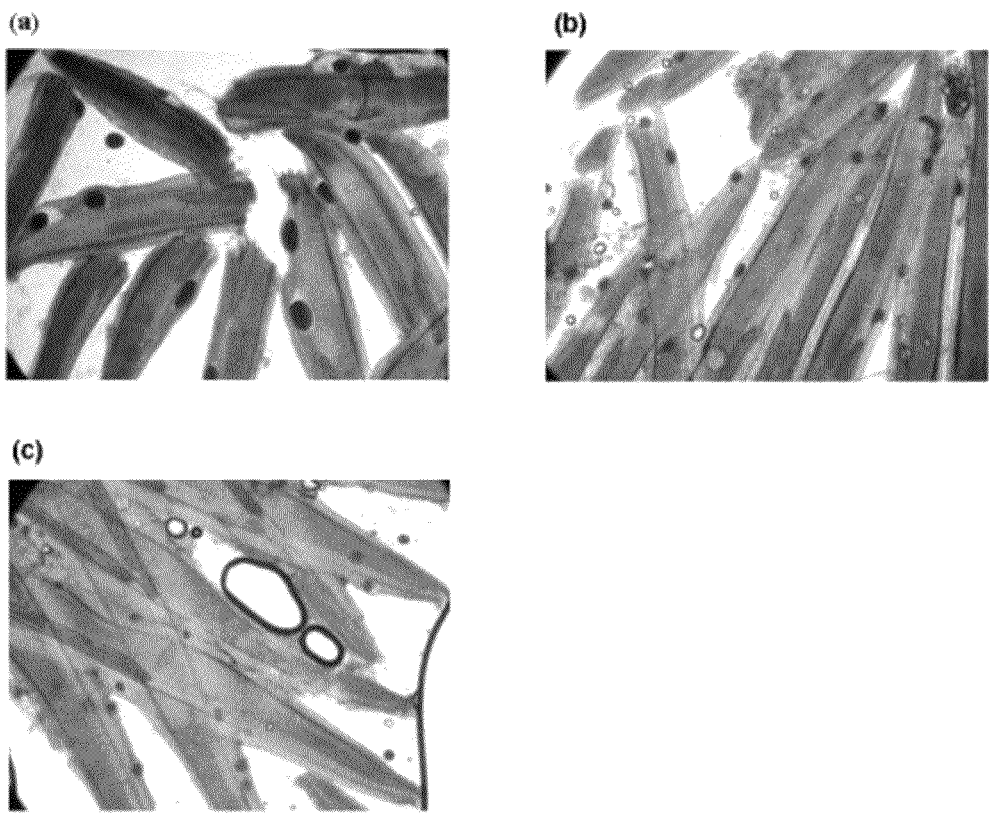
FIG. 2 is a photo of the ciliate protozoa parasitizing to the gills of *Pagrus major* three days after the exposure in each plot of Example 2. The long, slender ones are the gills, and the round to elliptical black shapes that appear to be attached thereto are the ciliate protozoa. In the figure, (a) shows a control plot in which no drug added feed was fed, (b) shows a plot where 216 mg sulfadimethoxine and 24 mg trimethoprim/kg body weight/day was orally administered for three days, (c) shows a plot in which 429 mg sulfamethoxazole and 86 mg trimethoprim/kg body weight/day was orally administered for three days.
Figure 3:
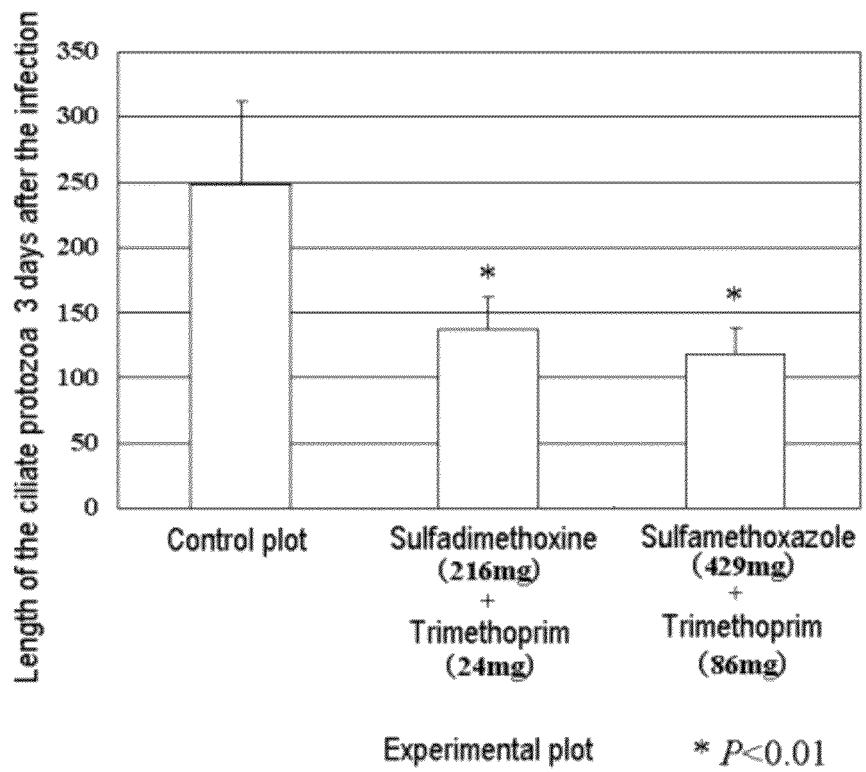
FIG. 3 is a figure of the results of Example 2, showing a comparison of the body lengths of the parasites three days after the exposure.

The results are shown in FIG. 2 and FIG. 3. The body lengths of the parasites for the sulfadimethoxine and trimethoprim administration plot and the sulfamethoxazole and trimethoprim administration plot were significantly smaller than the body length of the parasites in the control plot ($P<0.01$), and the growth thereof had been hindered. Thus, the results of Example 1 were reproduced. In addition, the movement of the parasites in the medicated plots was clearly affected by the drug, being torpid in comparison to those of the control plot.

Example 3

Parasiticidal Effect of the Oral Administration of an Inhibitor of Folate Synthesis and an Inhibitor of Folate Activation on the Parasitism of *Cryptocaryon irritans* on *Pagrus major* (3)

Test method: Fifty-six *Pagrus major* with an average weight of 91 g were reared for approximately 12 days in a 500-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 500-liter aquarium was stopped and approximately 500,000 *Cryptocaryon irritans* hatched larva were put into the aquarium, then the fish were exposed to the parasites for 1 hour. After exposure, seven fish each were moved into eight 100-liter aquariums. During the rearing period, 1.4 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the body length of the *Cryptocaryon irritans* parasitizing the gills was measured.

Experimental plot: A plot in which 300 mg sulfamethoxazole (SMXZ)/kg body weight/day, a plot in which 300 mg sulfadimethoxine (SDMX)/kg body weight/day, a plot in which 300 mg sulfamonomethoxine (SMMX)/kg body weight/day, a plot in which 300 mg sulfamerazine (SMDN)/kg body weight/day, a plot in which 300 mg sulfisomidine (SID)/kg body weight/day, a plot in which 300 mg sulfamethizole (SMZ)/kg body weight/day, a plot in which 300 mg sulfisozole (SIZ)/kg body weight/day were each orally administered for three days, and a control plot in which drug additive-free feed was fed were set up for a total of 8 plots. Test feeds were prepared by mixing a predetermined amount of each drug into moist feed.

Assessment of the effect: The body lengths of the parasites parasitizing the gills were compared.

Note that these results will be mentioned later together with Example 4.

Example 4

Parasiticidal Effect of the Oral Administration of an Inhibitor of Folate Synthesis and an Inhibitor of Folate Activation on the Parasitism of *Cryptocaryon irritans* on *Pagrus major* (4)

Test method: Forty-two *Pagrus major* with an average weight of 113.5 g were reared for approximately 12 days in a 500-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 500-liter aquarium was stopped and approximately 500,000 *Cryptocaryon irritans* hatched larva were put into the aquarium, then the fish were exposed to the parasites for 1 hour. After exposure, seven fish each were moved into six 100-liter aquariums. During the rearing period, 1.4 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the body lengths of the *Cryptocaryon irritans* parasitizing the gills was measured.

Experimental plot: A plot in which 60 mg trimethoprim (TMP)/kg body weight/day, a plot in which 60 mg methotrexate (MTX)/kg body weight/day, a plot in which 60 mg pyrimethamine (PRY)/kg body weight/day, a plot in which 60 mg isethionic acid pentamidine salt (PMD)/kg body weight/day, a plot in which a combination of 216 mg sulfadimethoxine/kg body weight/day and 24 mg trimethoprim/kg body weight/day were each orally administered for three days, and a control plot in which drug additive-free feed was fed were set up. Test feeds were prepared by mixing a predetermined amount of each drug into moist feed.

Assessment of the effect: The body lengths of the parasites parasitizing the gills were compared.

Figure 4:
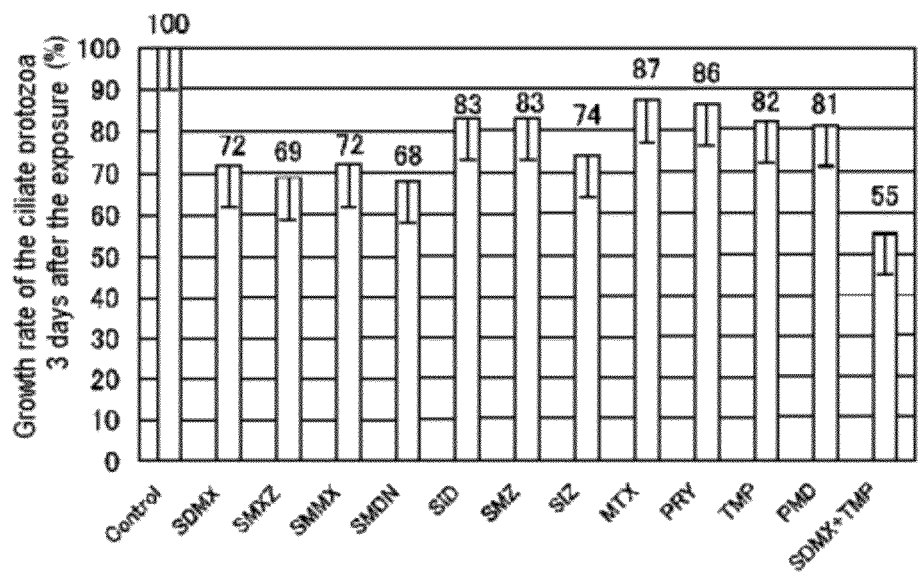
FIG. 4 is a figure showing the growth rate of parasites in each plot in Examples 3 and 4. The body lengths were compared and expressed as a percentage of the body length of control plot. The body lengths of 60 parasites were measured from each plot.

The results of Examples 3 and 4 are shown in FIG. 4. The body lengths of the parasites in all plots in which the drugs were administered are significantly smaller than the body lengths of the parasites in the control plot ($P<0.01$), and the growth thereof has been hindered. Furthermore, the movement of the parasites in all of the medicated plots was observed to be torpid in comparison to that in the control plot. This shows the parasites were affected by the drugs, and the functions for maintenance of life deteriorated. The result of the preceding Example 1 in addition to the results of these Examples 3 and 4 show the extent of the adverse effects on the vital activity of the *Cryptocaryon irritans*, wherein the inhibitor of folate synthesis as well as the inhibitor of folate activation hinder the growth of these parasites in common. Thus, it has become clear that the parasites synthesize folic acid themselves, and the drugs are able to suppress the growth of these parasites by hindering synthesis thereof. In addition, the growth of the parasites was hindered more in the plot in which the combination preparation of an inhibitor of folate synthesis (sulfadimethoxine) and an inhibitor of folate activation (trimethoprim) was administered than the plots in which either an inhibitor of folate synthesis or an inhibitor of folate activation was administered alone. Thus, for this parasite exterminator, it was concluded that the administration of a combination preparation of an inhibitor of folate synthesis and an inhibitor of folate activation provides a stronger parasiticidal effect than the administration of an inhibitor of folate synthesis or an inhibitor of folate activation alone.

Example 5

Parasiticidal Effect of the Oral Administration of an Inhibitor of Folate Synthesis and an Inhibitor of Olate Activation on the Parasitism of *Cryptocaryon irritans* on *Pagrus major* (5)

Figure 5:
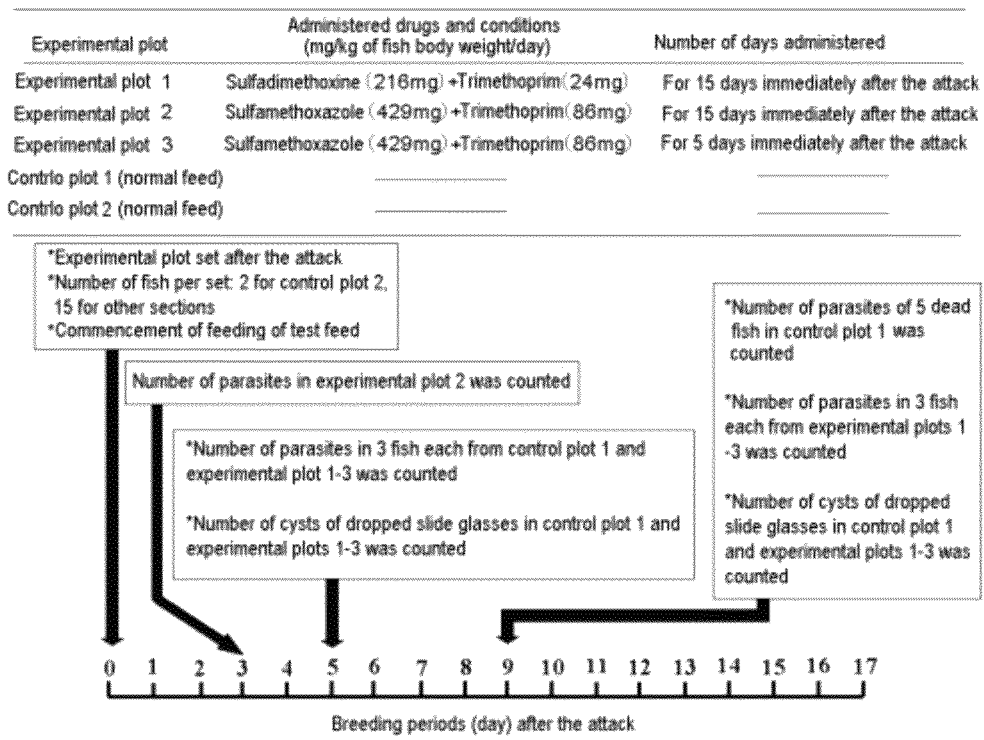
FIG. 5 is a figure showing an outline of the trial in Example 5.

Test method: Sixty-two *Pagrus major* with an average weight of 32 g were reared for approximately 7 days in a 200-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 200-liter aquarium was stopped and approximately 200,000 *Cryptocaryon irritans* hatched larva were put into the aquarium, then the fish were exposed to the parasites for 1 hour. After exposure, fifteen fish each were moved into four 100-liter aquariums. To observe the condition of the formation of cysts in each plot, six sheets of slide glass were dropped beforehand into these 100-liter aquariums. In addition, the remaining two fish were moved into a 100-liter aquarium in order to investigate the three days after the exposure condition of parasitic infection. During the rearing period, 1.2 liters/min. of seawater was supplied. An outline of the trial is shown in FIG. 5. A plot in which the test feed containing the drug was fed for five consecutive days after exposure and a plot in which the administration was for fifteen consecutive days was set up, and the feeding rate of the test feed was 2 wt % of fish body weight daily. The two fish in the plot for investigating the condition of the parasitic infection were sampled three days after the exposure, and the number of *Cryptocaryon irritans* parasitizing the left gills was counted. Then, three fish from each plot were sampled after five days following the exposure, and the number of *Cryptocaryon irritans* parasitizing the left gills was counted. To gain an understanding of the situation of the cyst formation, the dropped slide glasses were collected, and the number of cysts adhering thereto was counted at the same time. To examine whether these cysts would hatch, we dropped a slide glass to which cysts were attached into a 300 ml beaker containing seawater and observed it for 12 days. In order to continue to gain a further understanding of cyst formation, six slide glasses were placed into each plot again. The fish continued to be reared for up to 23 days after the exposure. Then the number of *Cryptocaryon irritans* parasitizing the left gills of all the fish that had died during the rearing period were counted. Furthermore, whenever a large number of fish were found to have died in any plot, three fish each were sampled from all of the other plots, and the number of *Cryptocaryon irritans* parasitizing the left gills was counted. Moreover, at the same time, the number of cysts collected from the slide glasses that had been placed into the water was counted. Another six slide glasses were placed into the plots in which rearing continued in order to ascertain the state of cyst formation.

Experimental plot: Test feeds were prepared by mixing a predetermined amount of each drug shown in FIG. 5 into moist feed. In addition, after the conclusion of the period of drug administration, drug additive-free feed was given in the medicated plots, just as it was given in the control plot.

Assessment of the effect: Comparison of the number of instances of parasitism, the number of cyst formations, the body length of the cysts, the presence/absence of hatched cysts, and the number of dead fish was performed.

Figure 6:
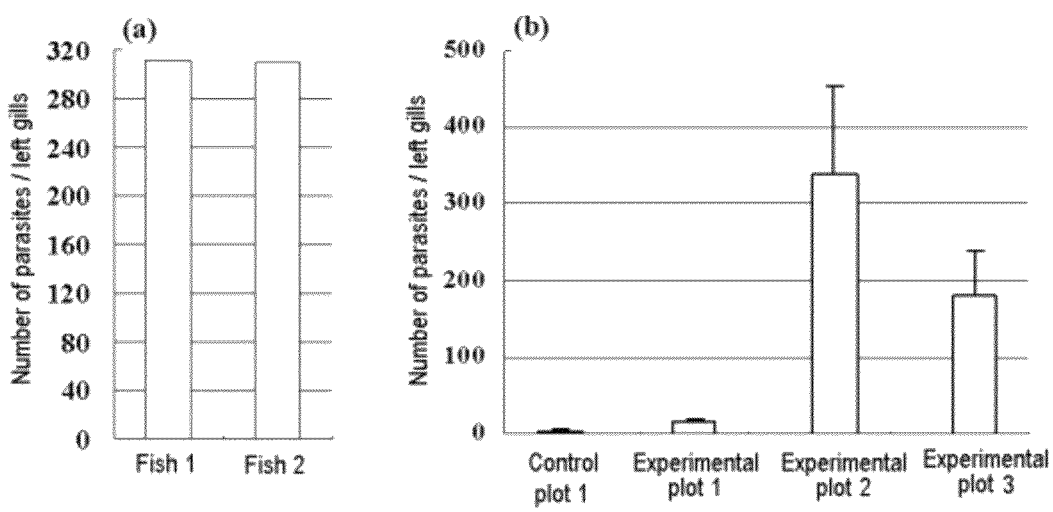
FIG. 6 (*a*) is a figure showing the number of parasites three days after the exposure in control plot 2 in Example 5.
Figure 7:
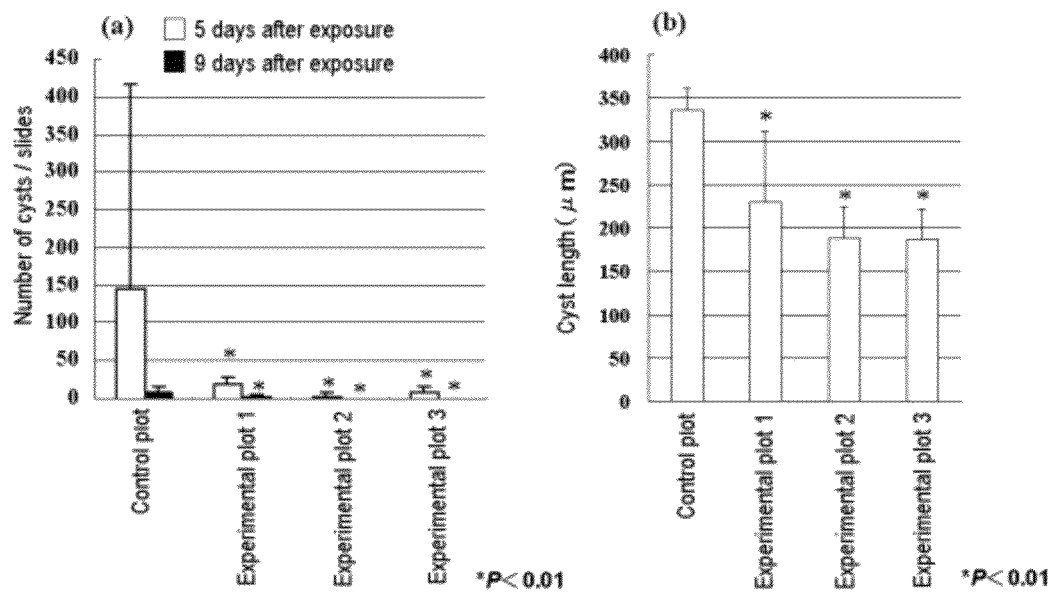
FIG. 7 is a figure showing a comparison of (a) the number of cysts and (b) the size of the cysts in each plot in Example 5.

The number of instances of parasitism on the left gills three days after the exposure in the plot for investigating the condition of the parasitic infection (control plot 2) was approximately 300 parasites (FIG. 6*a*). This result shows that the *Cryptocaryon irritans* infection in this trial was achieved as intended. FIG. 6*b* shows the number of these parasites in each plot five days after the exposure. The number of instances of parasitism in the control plot was essentially 0. FIG. 7*a* shows the results of the number of cyst formations five days and nine days after the exposure. The number of cysts that were formed in the control plot was clearly more numerous than in other plots, and it is likely that the parasites that became cysts left the host gills to become cysts. The number of these parasites in experimental plot 1 was low, just like that of the control plot. However, the number of resultant cyst formations clearly was fewer than in the control plot (P<0.01). It is therefore likely that the parasites in experimental plot 1 died out before becoming cysts. Thus, it has become apparent that the administration of sulfadimethoxine and trimethoprim clearly has parasiticidal effect. On the other hand, the number of instances of parasitism in experimental plots 2 and 3 are clearly numerous, and it is surmised that the withdrawal from the host was slow because the growth of these parasites had been hindered. Although few in number in plots other than control plot 1 (P<0.01), cyst formation nevertheless was detected. The body length of the cysts in the medicated plots was clearly shorter than that of the control plot (FIG. 7*b*). In addition, upon examining the hatching rate of these cysts, which was observed for twelve days, the control plot was 100%, the test 1 was 95.8%, test 2 was 35%, and test 3 was 45.2%. The number of days until hatching was three for control plot 1, eight to ten for experimental plot 1, and ten to twelve for experimental plots 2 and 3. Thus, it is clear that these drugs are hindering the normal development of the cysts even after the protozoan cysts have been formed.

Figure 8:
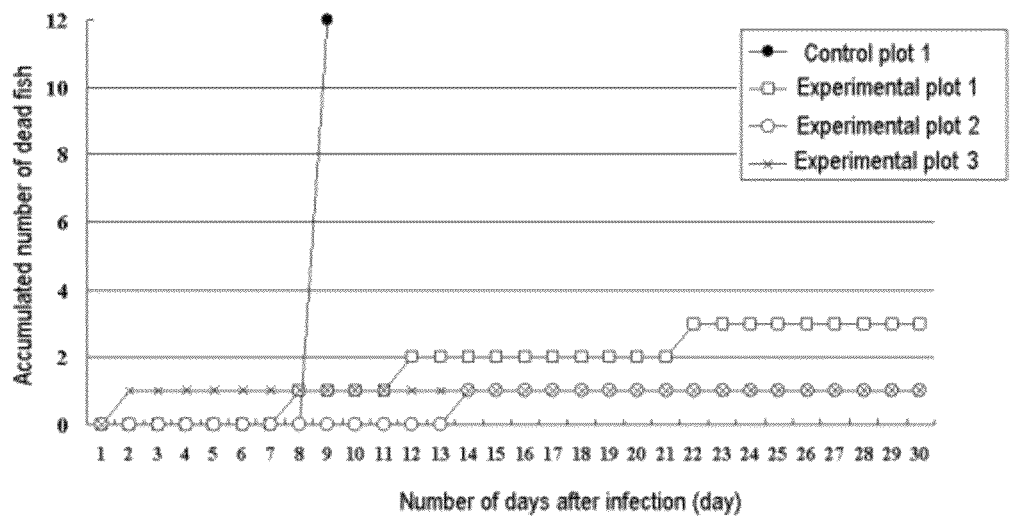
FIG. 8 is a figure showing a comparison of the number of dead fish in each plot in Example 5.

All of the test fish died in the control plot nine days after the exposure (FIG. 8). Upon investigating the number of instances of parasitism of these parasites on the left gills, more than 1,000 *Cryptocaryon irritans* had become parasitic. This is believed to be due to the reinfection by larva that had hatched from cysts. Three fish each from experimental plots 1, 2, and 3 were sampled nine days after the exposure, and upon investigating the number of instances of parasitism on the left gills, the parasitism by these parasites was not found in any of the fish. This is believed to be because the number of cysts was few and the normal development of the cysts had been hindered, so that new larvae were not hatching. FIG. 7*a* shows the results of the number of cysts formed nine days after the exposure. The number of cysts in experimental plots 2 and 3 was roughly 0. In experimental plots 2 and 3, the number of instances of parasitism of these parasites on the gills was observed to be numerous five days after the exposure, but no instances of parasitism of these parasites on the gills was observed nine days after the exposure, and the number of cysts that were formed nine days after the exposure was roughly 0, so it is accordingly believed that these parasites that had been parasitic died between five and nine days after exposure. Thus, it has been elucidated that the administration of sulfamethoxazole and trimethoprim has a parasiticidal effect.

Thereafter, the fish in experimental plots 1 to 3 continued to be kept for thirty days after the commencement of the trial. During a rearing period, the death of three fish in experimental plot 1, one fish in experimental plot 2, and one fish in experimental plot 3 occurred. Upon observing the gills of the dead fish, no *Cryptocaryon irritans* were detected. All of the dead fish had lost both eyes, and the cause of death was determined as cannibalism. All of the fish were sampled when the rearing period terminated, and the gills were observed, but no parasitism of *Cryptocaryon irritans* was found in any of the plots (experimental plots 1 to 3). At the same time, the slide glasses were collected, and the presence or absence of cysts was checked, but no cysts were observed. Thus, the surviving fish in experimental plots 1 to 3 are believed to have been totally cured of all *Cryptocaryon irritans* infection.

Accordingly, the inhibitor of folate synthesis and the inhibitor of folate activation not only hinder the growth of these parasites but also have a parasiticidal effect on these parasites, and it has been elucidated that they continue to act even after the formation of cysts, having an effect of hindering the normal development of the cysts.

Example 6

Parasiticidal Effect of the Oral Administration of a Combination Preparation Composed of an Inhibitor of Folate Synthesis and an Inhibitor of Folate Activation on the Parasitism of *Cryptocaryon irritans* in Pagrus major Test method: One hundred three *Pagrus major* with an average weight of 62 g were reared for approximately 13 days in a 500-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. Seawater supply was set at 2.4 liters per minute. For the parasitic infection, the seawater supply to the 500-liter aquarium was stopped and approximately 600,000 *Cryptocaryon irritans* hatched larva were put into the aquarium, then the fish were exposed to the parasites for 1 hour. After exposure, twenty fish each were moved into five 100-liter aquariums. In addition, the remaining three fish were moved into a 100-liter aquarium in order to investigate the condition of parasitic infection three days after the exposure. During the rearing period, 1.2 liters/min. of seawater was supplied. Test feed containing the drug was fed for five consecutive days, and the feeding times thereof were 2 hours after moving the fish to the 100-liter aquariums following the exposure to the larvae, as well as on Day 1, Day 2, Day 3, and Day 4 after the exposure. The feeding rate of the test feed was 2 wt % of fish body weight daily. The three fish in the plot for investigating the condition of the parasitic infection were sampled three days after the exposure, and the number of *Cryptocaryon irritans* parasitizing the left gills was counted. Four test fish from each plot were sampled five days after the exposure, and the number of *Cryptocaryon irritans* parasitizing the left gills was counted. In addition, the size of the parasites was observed at the same time.

The fish continued to be kept up to twenty-seven days after the exposure. The number of *Cryptocaryon irritans* parasitizing the left gills of all of the dead fish during the rearing period was counted. In addition, whenever a large number of fish died in any of the plots, wherein these parasites were believed to be the cause of death, three fish from every other plot were sampled, and the number of *Cryptocaryon irritans* parasitizing the left gills was counted.

Experimental plot: A plot in which a mixture of 125 mg sulfamethoxazole/kg body weight/day and 25 mg trimethoprim/kg body weight/day was orally administered for five days, a plot in which a mixture of 112.5 mg sulfamonomethoxine/kg body weight/day and 37.5 mg ormetoprim/kg body weight/day was orally administered for five days, a plot in which a mixture of 135 mg sulfadimethoxine/kg body weight/day and 15 mg trimethoprim/kg body weight/day was orally administered for five days, a plot in which a mixture of 136.4 mg sulfadimethoxine/kg body weight/day and 13.6 mg pyrimethamine/kg body weight/day was orally administered for five days, and a non-medicated plot in which drug additive-free feed was fed were set up. The drug dosage in the combination preparation administration plots was set at 150 mg the combination preparation/kg body weight/day. Test feeds were prepared by mixing a predetermined amount of each drug into moist feed.

Assessment of the effect: Comparisons of the number of instances of parasitism, the parasite formation, the cyst formation, and the number of dead fish were made.

Figure 9:
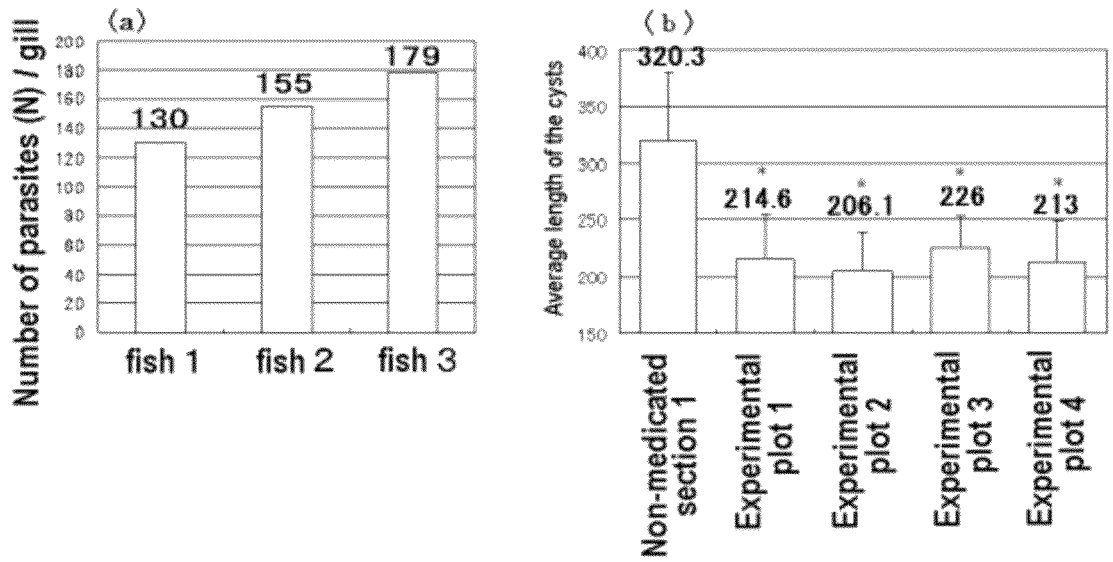
FIG. 9 is a figure showing (a) the number of parasites three days after the exposure in control plot 2 in Example 6.

The average number of instances of parasitism on the left gills of three *Pagrus major* three days after the exposure in the plot for investigating the condition of the parasitic infection was 155 parasites per fish (FIG. 9a). These results show that *Cryptocaryon irritans* infection was achieved as intended in this trial. In addition, the average body length of sixty parasites parasitizing the gills was 204 µm. One *Pagrus major* in the non-medicated plot died three days after the exposure. The number of instances of parasitism by these parasites on the left gills was 180 parasites, which was not a number of instances of parasitism that would lead to death. The dead fish had lost its left eye, and the cause of death was determined to be cannibalism.

The number of instances of parasitism by these parasites in each plot five days after the exposure was zero parasites in the non-medicated plot, three parasites in experimental plot 1, one parasite in experimental plot 2, zero parasites in experimental plot 3, and two parasites in experimental plot 4. Accordingly, it is believed that these parasites left the host gills to become cysts in all of the plots.

A comparison of the results of the body length of thirty cysts in each plot that had left the host five days after the exposure is shown in FIG. 9b. The average diameter of the cysts in the non-medicated plot was approximately 320 µm. The average diameter of the cysts in experimental plot 1 was 215 µm, the average body length of the cysts in experimental plot 2 was 206 µm, the average body length of the cysts in experimental plot 3 was 226 µm, and the average body length of the cysts in experimental plot 4 was 213 µm. The body length of the cysts in all of the medicated plots was significantly shorter than that in the control plot, and these parasites were affected by the drug only as they became cysts, to the extent that the growth thereof was hindered.

Seven days after the exposure, one *Pagrus major* each died in the non-medicated plot, experimental plot 2, and experimental plot 4. The number of instances of parasitism by these parasites on the left gills is eight for the fish died in the non-medicated plot, and zero for the fish died in experimental plot 2 and experimental plot 4. All of the dead fish had lost both of their eyes, therefore the cause of death was determined to be cannibalism.

Figure 10:
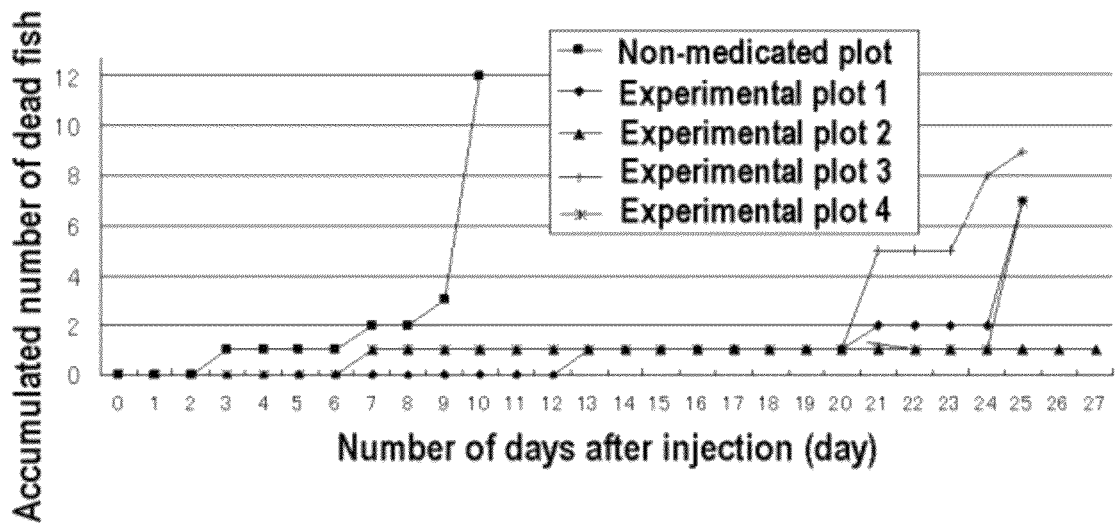
FIG. 10 is a figure showing a comparison of the number of dead fish in each plot in Example 6.

In the non-medicated plot, test fish began to die nine days after the exposure (FIG. 10). Upon examining the number of instances of parasitism by these parasites on the left gills of the test fish that died nine days after the exposure, more than 1,000 *Cryptocaryon irritans* were found to be parasitic. This is believed to be due to reinfection by larvae that had hatched from the cysts. Three fish each were sampled from experimental plots 1, 2, 3, and 4 nine days after the exposure, and upon examining the number of instances of parasitism on the left gills, it was found that no instances of parasitism by the parasites was found in any of the fish. The test fish in the non-medicated plot all died off by ten days after exposure. Afterward, the fish in experimental plots 1 to 4 continued to be kept for twenty-seven days after the commencement of the trial.

One *Pagrus major* each died in experimental plot 1 and experimental plot 3 thirteen days after the exposure. The number of instances of parasitism by these parasites on the left gills is six for the fish died in experimental plot 1, and twenty-three for the fish died in experimental plot 3. The dead fish had lost both eyes, and the cause of death was determined to be cannibalism.

Three test fish each were sampled from experimental plots 1 to 4 fifteen days after the exposure, and upon examining the number of instances of parasitism by these parasites on the left gills, the average number of parasites was five in experimental plot 1, one parasite in experimental plot 2, 6.3 parasites in experimental plot 3, and 3.7 parasites in experimental plot 4.

One *Pagrus major* died in experimental plot 1 twenty-one days after the exposure. The number of instances of parasitism by these parasites on the left gills was 54 parasites. The dead fish lost both eyes, and the cause of death was determined to be cannibalism. On the same day, four *Pagrus major* died in experimental plot 3. Among these four fish, two fish lost both eyes, one fish lost its left eye, and cloudy eyes and red skin, which are symptoms of *Cryptocaryon irritans* infection, were observed in one fish. The number of instances of parasitism by these parasites on the left gills of the dead fish was 788 parasites. The fish in which the symptoms of *Cryptocaryon irritans* infection were observed are surmised to have died due to *Cryptocaryon irritans* infection.

Three fish each were sampled from experimental plot 1, experimental plot 2, and experimental plot 4, and one fish was sampled from experimental plot 3 twenty-two days after the exposure, and upon investigating the number of instances of parasitism by these parasites on the left gills, an average of 9.3 parasites in experimental plot 1, nine parasites in experimental plot 2, 294 parasites in experimental plot 3, and 2.7 parasites in experimental plot 4 were found. Thereafter, three fish died in experimental plot 3 twenty-four days after the exposure, and all of the fish died in experimental plot 1, experimental plot 3, experimental plot 4 after twenty-five days. Parasitism by more than 1,000 of these parasites was found in all of the left gills. All six surviving fish in experimental plot 2 were sampled twenty-seven days after the exposure, thereby completing the trial. Parasitism by an average of more than 1,000 of these parasites was found in the left gills of the test fish that were examined.

From these results, it has become clear that all of the combination preparations that were tested had anti-ciliate protozoan action. Therein, it is believed that the combination of sulfamonomethoxine and ormetoprim in experimental plot 2 is the most effective. It is surmised that this is because of the combination of the drugs that were used as well as the difference in dosage of the inhibitor of folate synthesis and inhibitor of folate activation. The compounding ratio of the inhibitor of folate synthesis to the inhibitor of folate activation in this trial was 5:1 in experimental plot 1, 3:1 in experimental plot 2, 9:1 in experimental plot 3, and 10:1 in experimental plot 4. Thus, the compounds in which the proportion of the inhibitor of folate activation was larger are surmised to have a higher effectiveness against these parasites.

Example 7

Parasiticidal Effect Against the Parasitism of *Cryptocaryon irritans* on *Pagrus major* by Different Dosages of a Combination Preparation Composed of an Inhibitor of Folate Synthesis and an Inhibitor of Folate Activation Test method: One hundred four *Pagrus major* with an average weight of 38 g were reared for 19 days in a 500-liter aquarium and were acclimatized to a water temperature of 24.9° C. During that time, commercial feed (manufactured by Nippon Suisan Kaisha, Ltd.; early phase feed EP (expanded) pellets with a diameter of 2.5 mm) was given, and the feeding rate was 2.5 wt % of fish body weight daily. For the parasitic infection, the seawater supply to the 500-liter aquarium was stopped and approximately 600,000 *Cryptocaryon irritans* hatched larva were put into the aquarium, then the fish were exposed to the parasites for 1 hour. After exposure, twenty fish each were moved into five 100-liter aquariums. In addition, the remaining four fish were moved into a 100-liter aquarium in order to investigate the condition of parasitic infection three days after the exposure. 1.4 liters/min. of seawater was supplied. Test feed containing the drug was fed for five consecutive days, and the feeding times thereof were 2 hours after moving the fish to the 100-liter aquariums following the exposure to the larvae, as well as on Day 1, Day 2, Day 3, and Day 4 after the exposure. The feeding rate of the test feed was 2 wt % of fish body weight daily. The four fish in the plot for investigating the condition of the parasitic infection were sampled three days after the exposure, and the number of *Cryptocaryon irritans* parasitizing the left gills was counted. Five test fish from each plot were sampled five days after the exposure, and the number of *Cryptocaryon irritans* parasitizing the left gills was counted. In addition, the size of the parasites was observed at the same time.

The fish continued to be kept to twenty-nine days after the exposure. The numbers of *Cryptocaryon irritans* parasitizing the left gills of all of the dead fish during the rearing period were counted. In addition, whenever a large number of fish died in any of the plots, wherein these parasites were believed to be the cause of death, three fish from each of all the other plots were sampled, and the number of *Cryptocaryon irritans* parasitizing the left gills was counted.

Experimental plot: Experimental plot 1 (a plot in which a mixture of 37.5 mg sulfamonomethoxine/kg body weight/day and 12.5 mg ormetoprim/kg body weight/day was orally administered for five days (50 mg/kg of fish body weight per day, combined)), experimental plot 2 (a plot in which a mixture of 75 mg sulfamonomethoxine/kg body weight/day and 25 mg ormetoprim/kg body weight/day was orally administered for five days (100 mg/kg of fish body weight per day, combined)), experimental plot 3 (a plot in which a mixture of 187.5 mg sulfamonomethoxine/kg body weight/day and 62.5 mg ormetoprim/kg body weight/day was orally administered for five days (250 mg/kg of fish body weight per day, combined)), experimental plot 4 (a plot in which a mixture of 375 mg sulfamonomethoxine/kg body weight/day and 125 mg ormetoprim/kg body weight/day was orally administered for five days (500 mg/kg of fish body weight per day, combined)), and a control plot in which drug additive-free feed was fed were set up for a total of 5 plots. Test feeds were prepared by mixing a predetermined amount of each drug into moist feed.

Assessment of the effect: A comparison of the number of instances of parasitism, the parasite formation, the cyst formation, and the number of dead fish was performed.

Figure 11:
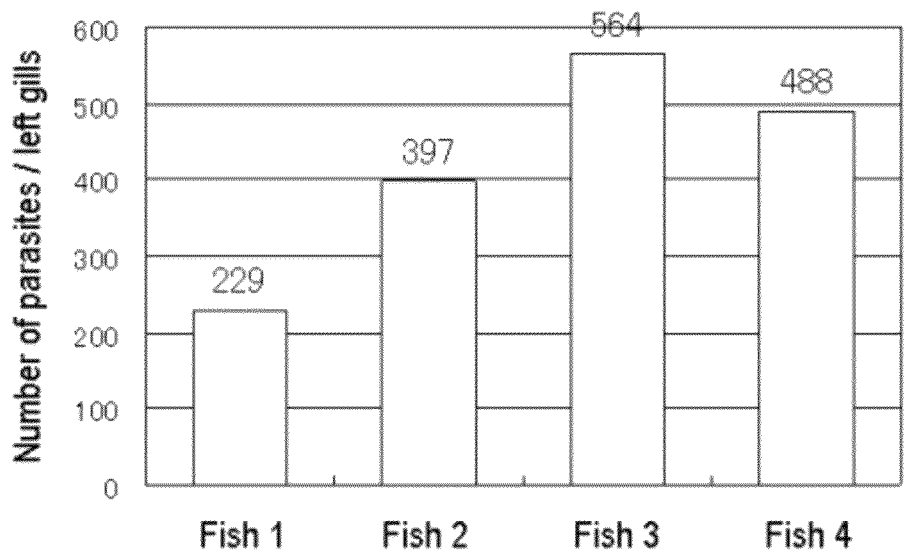
FIG. 11 is a figure showing the number of parasites three days after the exposure in control plot 2 in Example 7.

The average number of instances of parasitism on the left gills of the four *Pagrus major* three days after the exposure in the plot (control plot 2) for investigating the condition of the parasitic infection was 420 parasites per fish (FIG. 11). These results show that the *Cryptocaryon irritans* infection that was intended in this trial was achieved.

Figure 12:
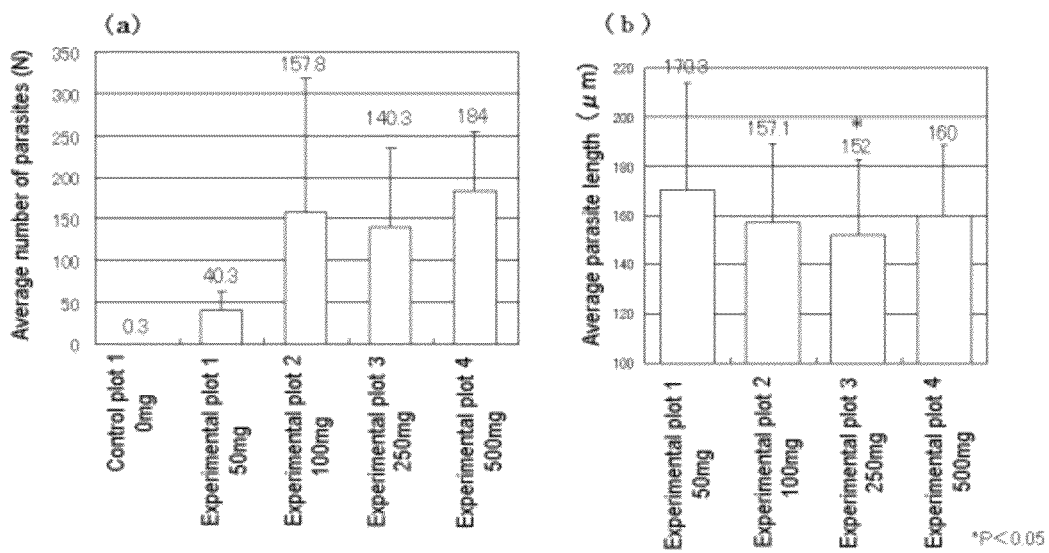
FIG. 12 (*a*) is a figure showing the mean number of parasites five days after the exposure in each plot in Example 7.

When the test feed was administered, the ingestion condition of the fish was observed. All of the test feed was consumed in the control plot as well as in experimental plot 1 to experimental plot 3, but in experimental plot 4 (a combined 500 mg/kg/kg body weight/day) some of the feed that had been consumed was found to have been expelled. This suggests that, when the dosage is comparatively large, with a combined 500 mg/kg/kg body weight/day, there is a possibility that adverse effects extended to the consumption of feed supplemented by this drug by the *Pagrus major*. The average number of *Cryptocaryon irritans* parasitizing the left gills of five fish in each plot five days after the exposure was approximately 0.3 parasites in the control plot, 40.3 in experimental plot 1, 157.8 in experimental plot 2, 140.3 in experimental plot 3, and 184 in experimental plot 4 (FIG. 12*a*). The body length of the parasites in experimental plot 1 to experimental plot 4 at this time is shown in FIG. 12*b*. In addition, when the cyst diameter (cyst length) of thirty cysts in each plot that were attached to the slide glasses that had been laid beforehand at the bottom of each aquarium were compared, they were approximately 320 μm in control plot, 215 μm in experimental plot 1, 206 μm in experimental plot 2, 226 μm in experimental plot 3, and 213 μm in experimental plot 4. These results show the resultant hindrance of growth of these parasites in all plots, from the relatively low dosage of 50 mg/kg/kg body weight/day to the relatively high dosage of 500 mg/kg/kg body weight/day, and that there is an effect of hindering withdrawal from the hosts to become cysts.

The change in number of *Cryptocaryon irritans* parasitizing the left gills of *Pagrus major* in each plot after exposure is shown in FIG. 13. In addition, FIG. 14 shows the change in number of deaths during the trial period. A large number of fish died in the control plot nine days after the exposure, and all of the fish had died by the tenth day. When the number of instances of parasitism by these parasites on the left gills was examined, more than 1,000 *Cryptocaryon irritans* were parasitic in each case. This is believed to be due to a re-infection by larvae hatched from cysts as in Example 5. Four fish each were sampled from experimental plots 1, 2, 3, and 4 nine days after the exposure, and when the number of instances of parasitism on the left gills was examined, the number of instances of parasitism by these parasites on all of the fish was zero. This is believed to be because the number of cysts was small, the normal development of the cysts was inhibited, and because the hatching of the larvae had been delayed.

One instance of the death of a fish occurred 12 days after the exposure in experimental plot 3. Upon observing the gills of the dead fish, no *Cryptocaryon irritans* could be detected. The dead fish had lost both eyes, and the cause of death was determined to be cannibalism. All of the test fish had died 18 days after the exposure in experimental plot 1. Upon examining the number of instances of parasitism by these parasites on the left gills of the dead fish, more than 1,000 *Cryptocaryon irritans* were found to be parasitic in every case. Three test fish were sampled from experimental plots 2, 3, and 4, and upon examining the number of instances of parasitism by these parasites on the left gills, an average of 74 parasites per fish were found in experimental plot 2, four parasites in experimental plot 3, and one parasite in experimental plot 4. Thereafter, the fish in experimental plots 1 to 4 continued to be kept for 29 days from the commencement of the trial.

One test fish died in experimental plot 2 21 days after the exposure, and all of the remaining fish died on the twenty-second day. The number of instances of parasitism by these parasites on the left gills of the test fish that died was approximately 1,000 parasites per fish.

Thereafter, the fish were continued to be reared 29 days after the exposure. All of the test fish in experimental plot 3 and experimental plot 4 that were surviving 29 days after the exposure were captured, and upon counting the number of instances of parasitism by these parasites on the left gills, an average of more than 1,000 *Cryptocaryon irritans* were observed per fish in experimental plot 3 and experimental plot 4. From the day on which all of the fish had died in the control plot, eight days passed until all of the fish had died in experimental plot 1 (combined dose of 50 mg/kg/kg body weight/day), twelve days passed for experimental plot 2 (combined dose of 100 mg/kg/kg body weight/day), and nineteen days passed for experimental plot 3 and experimental plot 4. These results show that the parasiticidal effect against parasites becomes higher, dependent on the dosage of the drug that is given.

Example 8

Parasiticidal Effect of a Combination Preparation Composed of an Inhibitor of Folate Synthesis and an Inhibitor of Folate Activation Against the Parasitism of *Cryptocaryon irritans* on *Takifugu rubripes*

Test method: Fifteen *Takifugu rubripes* with an average weight of 183 g were reared for 20 days in a 200-liter aquarium and were acclimatized to a water temperature of 25° C. During that time, commercial feed (manufactured by Nippon Suisan Kaisha, Ltd.; EP (expanded) pellets for *Takifugu rubripes* with a diameter of 3 mm) was given, and the feeding rate was 2 wt % of fish body weight daily. For the parasitic infection, the seawater supply to the 200-liter aquarium was stopped and approximately 200,000 *Cryptocaryon irritans* hatched larva were put into the aquarium, then the fish were exposed to the parasites for 1 hour. After exposure, five fish each were moved into three 100-liter aquariums. 1.4 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the number of *Cryptocaryon irritans* parasitizing the left gills was counted. In addition, the size of the parasites was observed and measured at the same time.

Experimental plot: A plot (SMMX+OMP plot) in which a combination of 112.5 mg sulfamonomethoxine/kg body weight/day and 37.5 mg ormetoprim/kg body weight/day was orally administered for three days, a plot (SDMX+PRY plot) in which a combination of 136.4 mg sulfadimethoxine/kg body weight/day and 13.6 mg pyrimethamine/kg body weight/day was orally administered for three days, and a control plot (Control plot) in which additive-free feed was fed were set up, for a total of 3 plots. Test feeds were prepared by mixing a predetermined amount of each drug into commercial EP feed. Furthermore, to add a uniform amount of drug to the bait, 5 wt % of water and 5 wt % of starch was added to the drug and mixed with feed.

Assessment of the effect: The number of instances of parasitism was compared, and the formation of parasites was observed.

Figure 15:
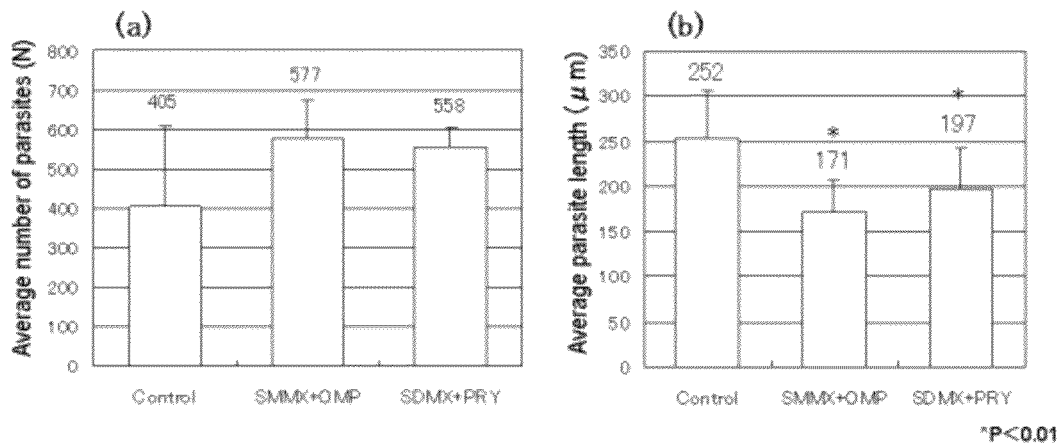
FIG. 15 (*a*) is a figure showing a comparison of the mean number of ciliate protozoan parasites on *Takifugu rubripes* three days after the exposure in each plot in Example 8.

As a result of having compared the number of instances of parasitism, the numbers of instances of parasitism in both of the medicated plots tended to be larger than that of the non-medicated control plot (FIG. 15a). The average number of instances of parasitism per gill was approximately 405 parasites in the control plot, approximately 544 parasites in the plot in which a combination of sulfamonomethoxine and ormetoprim was administered, and approximately 558 parasites in the plot in which a combination of sulfadimethoxine and pyrimethamine was administered, and both drugs hindered the withdrawal of the parasites from the hosts to become cysts.

In addition, as a result of having observed the parasite morphology, it was clear that the size of the parasites parasitizing the gills of the *Takifugu rubripes* in all of the medicated plots was significantly smaller than that of the control plot (FIG. 15b). The body length of the parasites was approximately 252 μm in the control plot, approximately 164 μm in the plot in which a combination of sulfamonomethoxine and ormetoprim was administered, and approximately 197 μm in the plot in which a combination of sulfadimethoxine and pyrimethamine was administered, and the growth of these parasites in all of the medicated plots had been hindered.

From these results, it became clear that a combination preparation of an inhibitor of folate synthesis and an inhibitor of folate activation showed anti-*Cryptocaryon irritans* action against the *Cryptocaryon irritans* infection of the *Takifugu rubripes*, similarly to the *Cryptocaryon irritans* infection of the *Pagrus major.*

Example 9

Parasiticidal Effect of the Combination Preparation Composed of an Inhibitor of Folate Synthesis and an Inhibitor of Folate Activation Against the Parasitism of *Cryptocaryon irritans* on *Paralichthys olivaceus*

Test method: Twenty-one *Paralichthys olivaceus* with an average weight of 47 g were reared for 8 days in a 200-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. 2.2 liters/min. of seawater was supplied. For the parasitic infection, the seawater supply to the 200-liter aquarium was stopped and approximately 200,000 *Cryptocaryon irritans* hatched larva were put into the aquarium, then the fish were exposed to the parasites for 1 hour. After exposure, seven fish each were moved into three 100-liter aquariums. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the number of *Cryptocaryon irritans* parasitizing the left gills was counted. In addition, the size of the parasites was observed at the same time.

Experimental plot: A plot (SMMX+OMP plot) in which a combination of 112.5 mg sulfamonomethoxine/kg body weight/day and 37.5 mg ormetoprim/kg body weight/day was orally administered for three days, a plot (SDMX+PRY plot) in which a combination of 136.4 mg sulfadimethoxine/kg body weight/day and 13.6 mg pyrimethamine/kg body weight/day was orally administered for three days, and a control plot (Control plot) in which additive-free feed was fed were set up for a total of 3 plots. Test feeds were prepared by mixing a predetermined amount of each drug into commercial EP feed. Furthermore, to add a uniform amount of drug to the bait, 5 wt % of water and 5 wt % of starch was added to the drug and mixed with feed.

Assessment of the effect: The number of instances of parasitism was compared, and the formation of parasites was observed.

Figure 16:
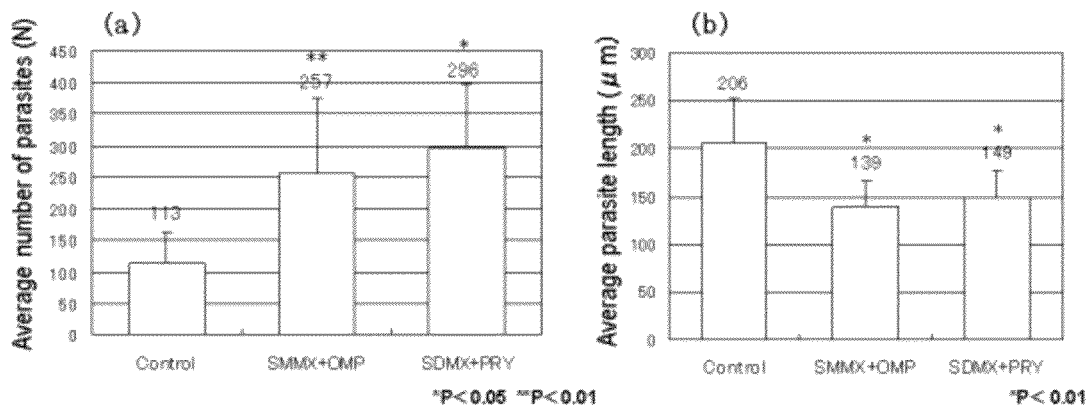
FIG. 16 (*a*) is a figure showing a comparison of the mean number of ciliate protozoan parasites on *Paralichthys olivaceus* three days after the exposure in each plot in Example 9.

As a result of having compared the number of instances of parasitism, the numbers of instances of parasitism in both of the medicated plots tended to be larger than that of the control plot (FIG. 16a). Both drugs had hindered the withdrawal of the parasites from the hosts to become cysts.

In addition, as a result of having observed the parasite morphology, it was clear that the size of the parasites parasitizing the gills of the *Paralichthys olivaceus* in all of the medicated plots was significantly smaller than those of the control plot (FIG. 16b).

From these results, it became clear that a combination preparation of an inhibitor of folate synthesis and an inhibitor of folate activation showed anti-ciliate protozoa action against the *Cryptocaryon irritans* infection of the *Paralichthys olivaceus*, similarly to the *Cryptocaryon irritans* infection of the *Pagrus major.*

Example 10

Parasiticidal Effect of the Combination Preparation Composed of an Inhibitor of Folate Synthesis and an Inhibitor of Folate Activation Against the Parasitism of *Cryptocaryon irritans* on *Seriola dumerili*

Test method: Twenty-four *Seriola dumerili* with an average weight of 26 g were reared for 7 days in a 200-liter aquarium and were acclimatized to a water temperature of 25° C. During that time, commercial feed (manufactured by Nippon Suisan Kaisha, Ltd.; early phase feed EP (expanded) pellets with a diameter of 2.5 mm) was given, and the feeding rate was 2 wt % of fish body weight daily. For the parasitic infection, the seawater supply to the 200-liter aquarium was stopped and approximately 200,000 *Cryptocaryon irritans* hatched larva were put into the aquarium, then the fish were exposed to the parasites for 1 hour. After exposure, eight fish each were moved into three 100-liter aquariums. 1.4 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the number of *Cryptocaryon irritans* parasitizing the left gills was counted. In addition, the size of the parasites was observed at the same time.

Experimental plot: A plot (SMMX+OMP plot) in which a combination of 112.5 mg sulfamonomethoxine/kg body weight/day and 37.5 mg ormetoprim/kg body weight/day was orally administered for three days, a plot (SDMX+PRY plot) in which a combination of 136.4 mg sulfadimethoxine/kg body weight/day and 13.6 mg pyrimethamine/kg body weight/day was orally administered for three days, and a control plot (Control plot) in which additive-free feed was fed were set up for a total of 3 plots. Test feeds were prepared by mixing a predetermined amount of each drug into commercial feed (manufactured by Nippon Suisan Kaisha, Ltd.; early phase feed EP (expanded) pellets with a diameter of 2.5 mm).

Furthermore, to add a uniform amount of drug to the bait, 5 wt % of water and 5 wt % of starch was added to the drug and mixed with feed.

Assessment of the effect: The number of instances of parasitism was compared, and the morphology of parasites was observed.

Figure 17:
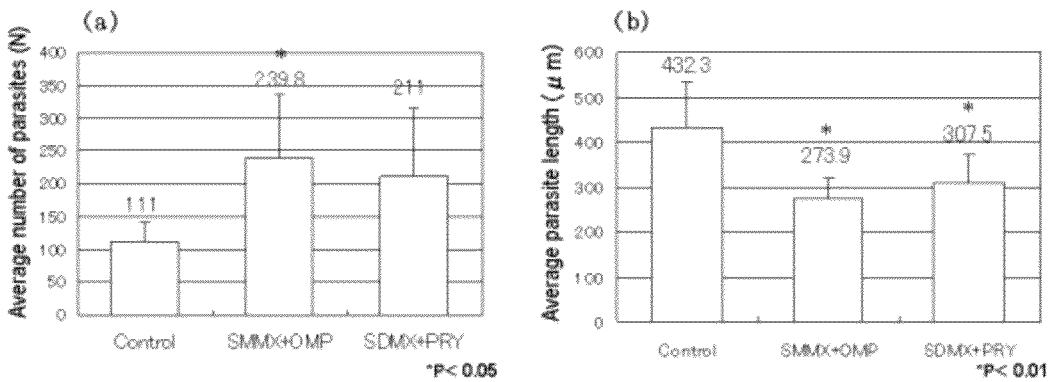
FIG. 17 (*a*) is a figure showing a comparison of the mean number of ciliate protozoan parasites on *Seriola dumerili* three days after the exposure in each plot in Example 10.

As a result of having compared the number of instances of parasitism, the number of instances of parasitism in both of the medicated plots tended to be larger than that of the control plot (FIG. 17a). Both drugs had hindered the withdrawal of the parasites from the hosts to become cysts.

In addition, as a result of having observed the parasite morphology, it was clear that the size of the parasites parasitizing the gills of the *Seriola dumerili* in all of the medicated plots was significantly smaller than that of the control plot (FIG. 17b).

From these results, it became clear that a combination preparation of an inhibitor of folate synthesis and an inhibitor of folate activation showed anti-ciliate protozoa action against the *Cryptocaryon irritans* infection of the *Seriola dumerili*, similarly to the *Cryptocaryon irritans* infection of the *Pagrus major*.

Example 11

Parasiticidal Effect of the Combination Preparation Composed of an Inhibitor of Folate Synthesis and an Inhibitor of Folate Activation Against the Parasitism of *Cryptocaryon irritans* on *Epinephelus septemfasciatus*

Test method: Twenty-one *Epinephelus septemfasciatus* with an average weight of 14 g were reared for 1 day in a 100-liter aquarium and were acclimatized to a water temperature of 25° C. During that time, commercial feed (manufactured by Nippon Suisan Kaisha, Ltd.; early phase feed EP (expanded) pellets with a diameter of 2 mm) was given, and the feeding rate was 3 wt % of fish body weight daily. For the parasitic infection, the seawater supply to the 100-liter aquarium was stopped and approximately 100,000 *Cryptocaryon irritans* hatched larva were put into the aquarium, then the fish were exposed to the parasites for 1 hour. After exposure, seven fish each were moved into three 100-liter aquariums. 1.4 liters/min. of seawater was supplied. Test feed containing the drug was fed for three consecutive days, and the feeding times thereof were 2 hours after moving the fish to the 100-liter aquariums following the exposure to the larvae, as well as on Day 1 and Day 2 after the exposure. The feeding rate of the test feed was 2 wt % of fish body weight daily. All of the fish were sampled three days after the exposure, and the number of *Cryptocaryon irritans* parasitizing the left gills was counted. In addition, the size of the parasites was observed at the same time.

Experimental plot: A plot (SMMX+OMP plot) in which a combination of 112.5 mg sulfamonomethoxine/kg body weight/day and 37.5 mg ormetoprim/kg body weight/day was orally administered for three days, a plot (SDMX+PRY plot) in which a combination of 136.4 mg sulfadimethoxine/kg body weight/day and 13.6 mg pyrimethamine/kg body weight/day was orally administered for three days, and a control plot (Control plot) in which additive-free feed was fed were set up, for a total of 3 plots. Test feeds were prepared by mixing a predetermined amount of each drug into commercial EP feed. Furthermore, to add a uniform amount of drug to the bait, 5 wt % of water and 5 wt % of starch was added to the drug and mixed with feed.

Assessment of the effect: The number of instances of parasitism was compared, and the morphology of parasites was observed.

Figure 18:
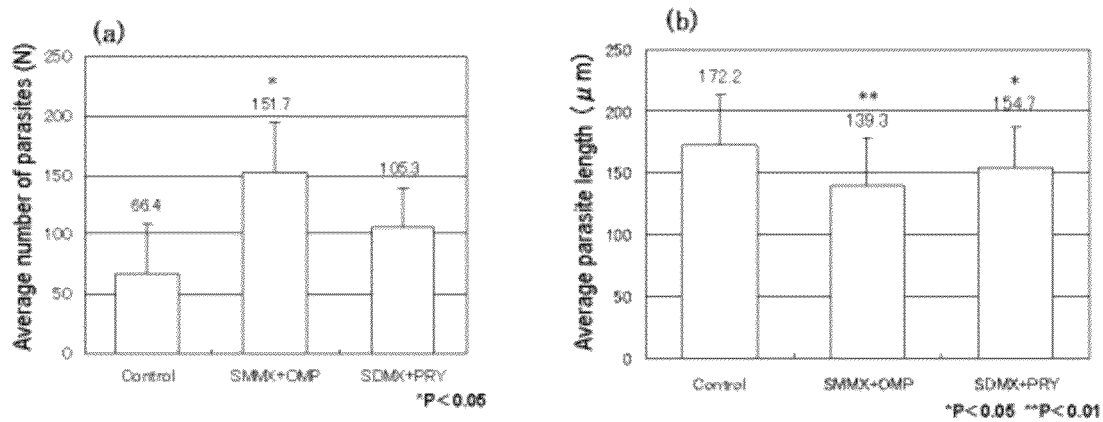
FIG. 18 (*a*) is a figure showing a comparison of the mean number of ciliate protozoan parasites on *Epinephelus septemfasciatus* three days after the exposure in each plot in Example 11.

As a result of having compared the number of instances of parasitism, the number of instances of parasitism in both of the medicated plots tended to be larger than that of the control plot (FIG. 18a). Both drugs had hindered the withdrawal of the parasites from the hosts to become cysts.

In addition, as a result of having observed the parasite morphology, it was clear that the size of the parasites parasitizing the gills of the *Epinephelus septemfasciatus* in all of the medicated plots was significantly smaller than that of the control plot (FIG. 18b).

From these results, it became clear that a combination preparation of an inhibitor of folate synthesis and an inhibitor of folate activation showed anti-ciliate protozoa action against the *Cryptocaryon irritans* infection of the *Epinephelus septemfasciatus*, similarly to the *Cryptocaryon irritans* infection of the *Pagrus major*.

From the above-mentioned results, it was clear that the inhibitor of folate synthesis and the inhibitor of folate activation together hinder the growth of the parasites and further hindered the development of the cysts. Thus, it became clear that the parasites synthesize folic acid themselves, and that by inhibiting such synthesis, it is possible to suppress the growth of the parasites and the parasitic activity thereof. In addition, a clear anti-ciliate protozoan action could be obtained by administering either an inhibitor of folate synthesis or an inhibitor of folate activation alone to the host fish, but it has been elucidated that a higher parasiticidal effect can be obtained by administering a combination preparation composed of an inhibitor of folate synthesis and an inhibitor of folate activation. A combination preparation composed of an inhibitor of folate synthesis and an inhibitor of folate activation displayed anti-ciliate protozoa action in all of the tested fish species, that is, *Pagrus major*, *Seriola dumerili*, and *Epinephelus septemfasciatus*, which are Perciformes fish, *Takifugu rubripes*, which are Tetraodontiformes, and *Paralichthys olivaceus*, which are Pleuronectiformes fish. Thus, an inhibitor of folate synthesis, an inhibitor of folate activation, and the combination thereof are thought to display anti-ciliate protozoa action against the *Cryptocaryon irritans* infection of various fish species.

Example 12

Parasiticidal Effect of the Combination Preparation Composed of an Inhibitor of Folate Synthesis and an Inhibitor of Folate Activation Against the Parasitism of *Ichthyophthirius multliis*

Test method: After eighteen *Carassius auratus auratus* with an average weight of 3.6 g were reared for 3 days in a 25-liter aquarium and were acclimatized to a water temperature of 21° C., they were reared together for 2 days with *Colisa labiosa* that were infected with *Ichthyophthirius multifiliis* and were secondary infected by *Ichthyophthirius multifiliis*, and afterward were used in an experiment in which only eight *Carassius auratus* auratus each were kept in two 25-liter aquariums that was newly set up. In order to verify the realization of infection, the number of parasites of the two remaining *Carassius auratus auratus* was investigated. The average number of instances of parasitism on the body surface per fish at that time was 66 parasites.

From the first day of infection, test feed containing the drugs was given to each experimental plot, while water was added to commercial feed (manufactured by Nippon Suisan Kaisha, Ltd.; early phase feed EP (expanded) pellets with a diameter of 2 mm) in the control plot. The amount that was fed was set at 0.7 wt % of the total body weight of the fish.

A combination of 112.5 mg sulfamonomethoxine/kg body weight/day and 37.5 mg ormetoprim/kg body weight/day (150 mg/kg/kg body weight/day, combined) was administered each day to the experimental plots.

For a determination of the effect, the number of parasites parasitizing the body surface of all test fish in each plot on the third and seventh days after commencement of the trial was visually counted. In addition, whenever fish died during the trial period, the number of parasites parasitizing the body surface was counted.

Figure 19:
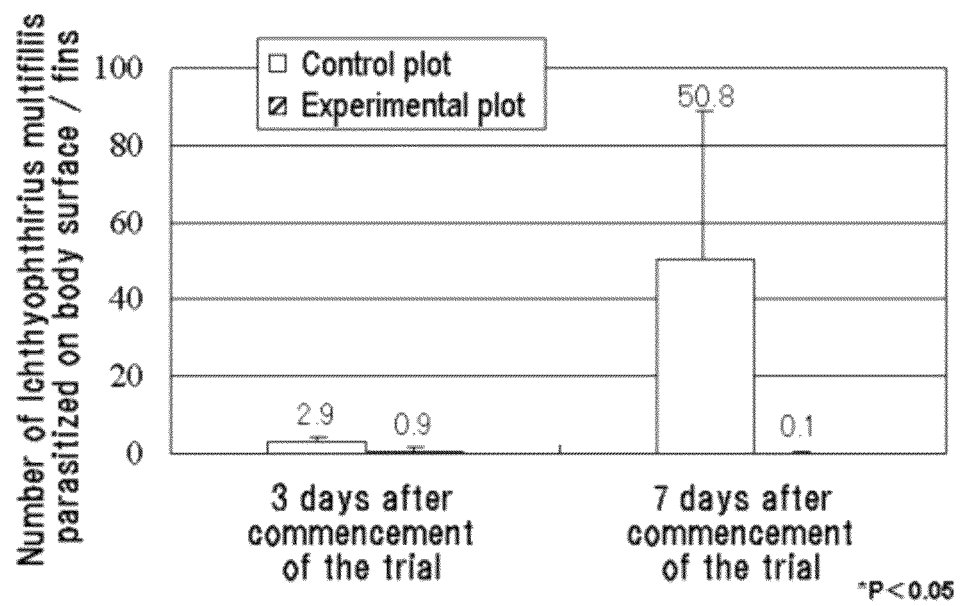
FIG. 19 is a figure showing a comparison of the number of parasites three and seven days after the exposure in each plot in Example 12.

The number of instances of parasitism by these parasites on the third day was 2.9 parasites on average in the control plot and 0.9 parasites on average in the experimental plots, and the number of instances of parasitism by these parasites on the seventh day was 50.8 parasites on average in the control plot and 0.1 parasites on average in the experimental plots (FIG. 19).

Figure 20:
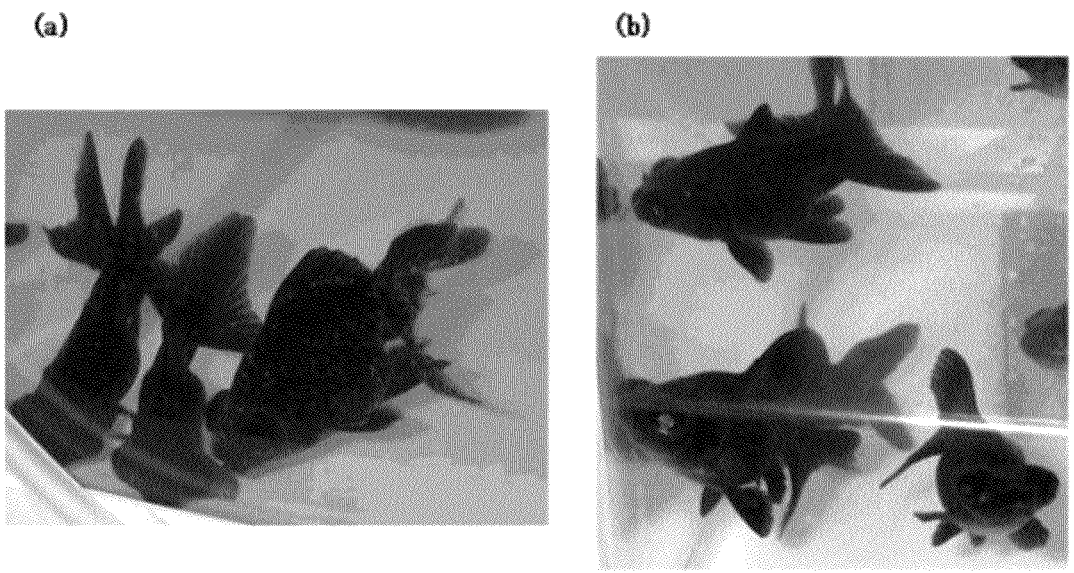
FIG. 20 is a figure in which the condition of parasitism on the *Ichthyophthirius multifiliis* test fish 9 days after the exposure has been photographed in Example 12. (a) shows the condition of 9 days after the exposure in control plot. Uncounted number of parasites is observed on the surface of the test fishes. (b) shows the condition 9 days after the exposure in the plot in which combination of SMMX and OMP was administered. Compared to the control plot, almost no parasites are observed.

The test fish in the control plot and the experimental plots on the ninth day after commencement of the test are shown in FIG. 20. At this point, the parasitism of countless *Ichthyophthirius multifiliis* was visually observed on test fish in the control plot. On the other hand, very little parasitism was detected in the test fish in the experimental plots.

All of the test fish had died out in the control plot on the eleventh day after commencement of the trial. Upon examining the body surface and fins of the dead fish, more than 2,000 parasites were observed, wherein the parasites had clearly multiplied. All of the test fish were captured in the experimental plots on the same day, and the body surfaces and fins were examined, but no parasitism by these parasites was detected. From these results, it is clear that the combination preparation composed of an inhibitor of folate synthesis and an inhibitor of folate activation have a parasiticidal effect against *Ichthyophthirius multifiliis*. Thus, it has become clear that *Ichthyophthirius multifiliis* also is a parasite that synthesizes folic acid itself, similarly to *Cryptocaryon irritans*, and that it is possible to suppress the growth and parasitic activity thereof by hindering such synthesis.

In the case of *Cryptocaryon irritans*, the combination preparation composed of an inhibitor of folate synthesis and an inhibitor of folate activation displayed anti-ciliate protozoa action in all of the fish species that were tested. Thus, the inhibitor of folate synthesis, the inhibitor of folate activation, and the combination thereof is believed to display anti-ciliate protozoa action against *Ichthyophthirius multifiliis* infection that occurs in various fish species.

Example 13

Parasiticidal Effect of the Administration of a Low Dosage Administration of a Combined Preparation Composed of an Inhibitor of Folate Synthesis and an Inhibitor of Folate Activation Against Parasitism of *Cryptocaryon irritans* in *Takifugu rubripes* (1)

Figure 21:
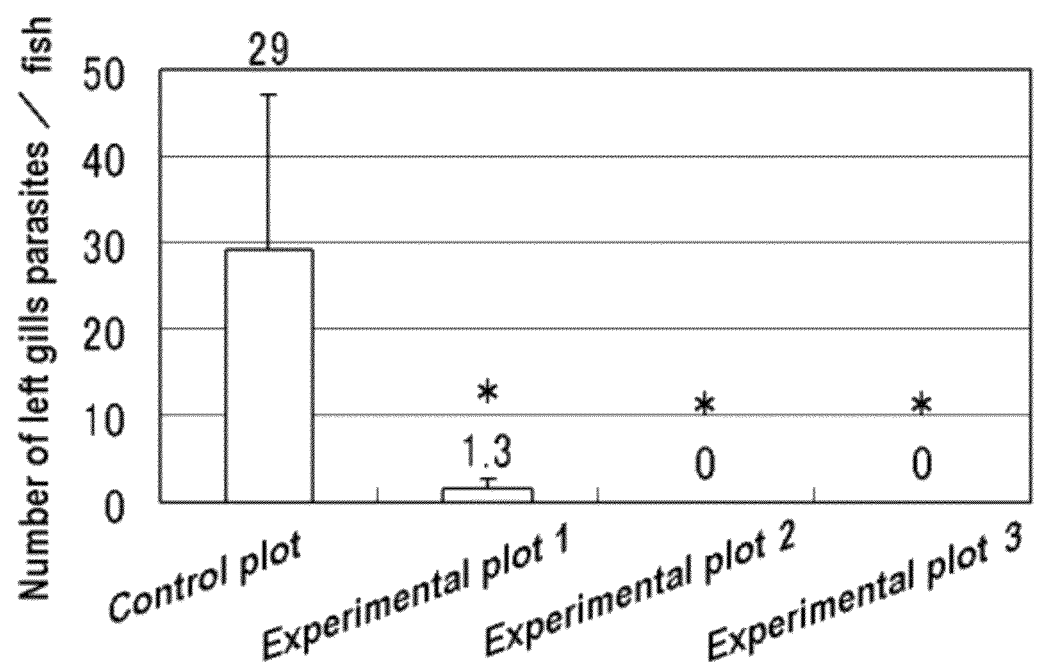
FIG. 21 is a figure showing the number of parasites in each plot of Example 13 fourteen days after the exposure.

Test method: Forty-eight *Takifugu rubripes* with an average weight of 130 g were reared for 13 days in a 500-liter aquarium and acclimatized to a water temperature of 24.5° C. During that time, commercial feed was given, and the feeding rate was 1.5 wt % of fish body weight daily. For the parasitic infection, the seawater supply to the 500-liter aquarium was stopped, approximately 200,000 hatched *Cryptocaryon irritans* larvae were put into the aquarium, and the fish were exposed to the parasites for 1 hour. After exposure, twelve fish each were transferred into four 100-liter aquariums. Seawater was supplied at a rate of 1.4 liters/min. Test feed containing the drugs was supplied for 14 consecutive days, starting at 2 hours after moving the fish to the 100-liter aquariums following the exposure to the larvae, then once every 24 hours until the thirteenth day after the exposure. The feeding rate of the test feed was 1% of fish body weight daily. Three fish from each plot were sampled 14 days after the exposure, and the number of *Cryptocaryon irritans* parasitizing the left gills was counted (FIG. 21).

The fish were raised continuously up to 28 days after the exposure, and the number of *Cryptocaryon irritans* parasitizing the left gills was counted for all dead fish during the culturing time interval. When a large number of deaths occurred in any of the plots, two fish each were also sampled from all of the other plots, and the number of *Cryptocaryon irritans* parasitizing the left gills was counted.

A total of four test plots were established: Test plot 1: Supplied with a mixture (25 mg/kg fish body weight per day as a combined preparation) of sulfamonomethoxine (18.75 mg/kg fish body weight per day) and ormetoprim (6.25 mg/kg fish body weight per day) orally administered for 14 days, Test plot 2: Supplied with a mixture (50 mg/kg fish body weight per day as a combined preparation) of sulfamonomethoxine (37.5 mg/kg fish body weight per day) and ormetoprim (12.5 mg/kg fish body weight per day) orally administered for 14 days, Test plot 3: Supplied with a mixture (150 mg/kg fish body weight per day as a combined preparation) of sulfamonomethoxine (112.5 mg/kg fish body weight per day) and ormetoprim (37.5 mg/kg fish body weight per day) orally administered for 14 days, and Test plot 4: A control plot supplied with drug additive-free feed. A predetermined amount of each drug was added to commercial EP feed to produce the test feed. In order to add the drug uniformly to the feed, 5% of the total feed amount each of water and starch were added to the drugs, the mixture was blended, and then the mixture was added to the feed.

Assessment of the effect: The numbers of parasites and dead fish count were compared.

The average number of parasites parasitizing the left gills of three fish in each plot on the fourteenth day after exposure was about 29 for the control plot, about 1.3 for Test plot 1, 0 for Test plot 2, and 0 for Test plot 3 (FIG. 21).

Figure 22:
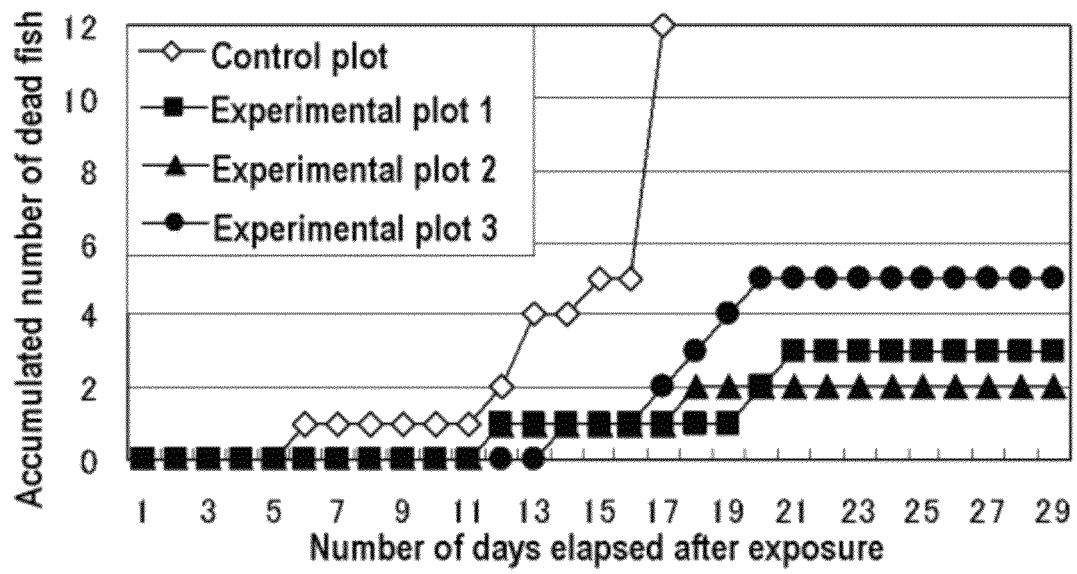
FIG. 22 is a figure showing the change in the numbers of dead fish during the test period for each plot in Example 13.
Figure 23:
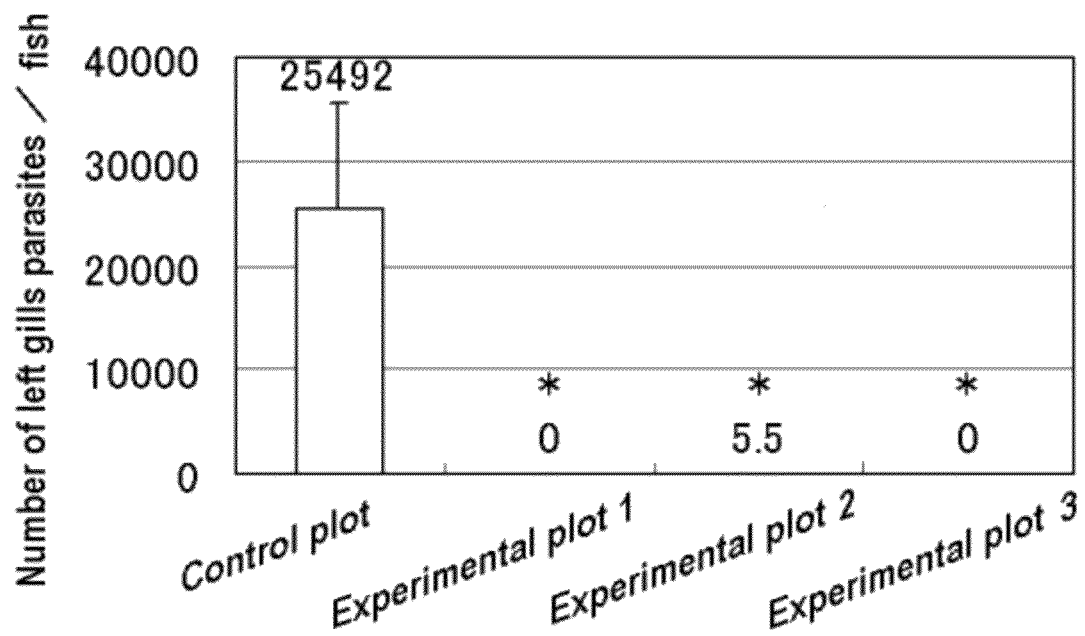
FIG. 23 is a figure showing the number of parasites in each plot of Example 13 fifteen days after the exposure.

FIG. 22 shows the change in number of dead fish during the trial period. A large number of the test fish in the control plot died due to *Cryptocaryon irritans* on the sixteenth day after exposure. Upon examination of the parasite count within the left gills of these dead fish, infection by over 1,000 parasites was found in each fish. This is thought to have been due to re-infection by larva hatching from cysts. On the sixteenth day after exposure, 2 fish each were sampled from test plot 1, test plot 2, and Test plot 3. The number of parasites of the left gills was counted. This value was 0 for Test plot 1, about 5.5 for Test plot 2, and 0 for test plot 3 (FIG. 23).

Thereafter, during the trial period up to the 28th day, 1 to 3 deaths occurred in each of the test plots. When the numbers of parasites of the left gills of the dead fish were counted, the number of *Cryptocaryon irritans* parasites in the left gills of the fish dead on the 22nd day was found to be just one for one fish in the Test plot 1. The total number of *Cryptocaryon irritans* parasites in the other dead fish was zero.

Based on these results, in all of the test plots, it was determined that nearly 100% of the *Cryptocaryon irritans* parasites were eliminated even when the dose was low (150 to 25 mg/kg of body weight) for the combined preparation formed from the inhibitor of folate synthesis and the inhibitor of folate activation.

Example 14

Parasiticidal Effect of the Administration of a Low Dosage of a Combined Preparation Composed of an Inhibitor of Folate Synthesis and an Inhibitor of Folate Activation Against Parasitism of *Cryptocaryon irritans* in *Takifugu rubripes* (2)

Test method: Six or seven fish each of an average weight of 160 g were raised for 8 days in three 100-liter aquariums and were acclimatized to a water temperature of 24.5° C. During that time, commercial feed was given at a rate of 1.5% of fish body weight daily. For the parasitic infection, the water supply to the three 100-liter aquariums was stopped, approximately 200,000 *Cryptocaryon irritans* hatched larva were put into the aquarium, and then the fish were exposed to the parasites for 1 hour. Then water was supplied at a rate of 1.4 liters/min. Test feed containing the drugs was supplied for 14 consecutive days, starting at 2 hours following the exposure to the larvae then once every 24 hours daily up to the thirteenth day after the exposure. The supply rate of the test feed was 1% of fish body weight daily. When a test fish died after exposure, the number of *Cryptocaryon irritans* infesting the left gill was counted.

A total of three test plots were established: Test plot 1: Supplied with a mixture (8 mg/kg fish body weight per day as a combined preparation) of sulfamonomethoxine (6 mg/kg fish body weight per day) and ormetoprim (2 mg/kg fish body weight per day) orally administered for 14 days, Test plot 2: Supplied with a mixture (24 mg/kg fish body weight per day as a combined preparation) of sulfamonomethoxine (18 mg/kg fish body weight per day) and ormetoprim (6 mg/kg fish body weight per day) orally administered for 14 days, and Test plot 3: A control plot supplied with drug additive-free feed. A predetermined amount of each drug was added to commercial EP feed to produce the test feed. In order to add the drug uniformly to the feed, 5% of the total feed amount each of water and starch were added to the drugs, the mixture was blended, and then the mixture was added to the feed.

Assessment of the effects: The number of parasites and dead fish were compared.

Figure 24:
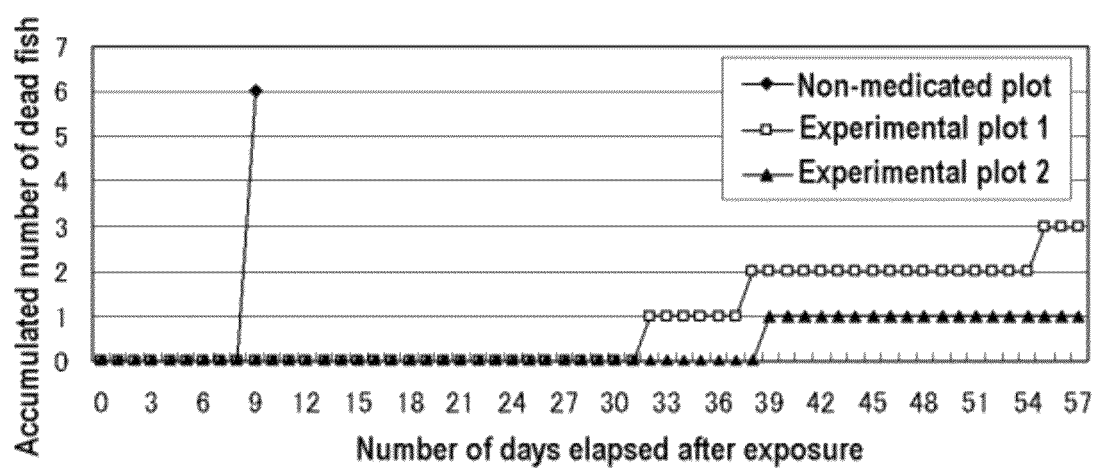
FIG. 24 is a figure showing the change in the numbers of dead fish during the test period for each plot in Example 14.

The change in number of deaths after exposure is shown in FIG. 24. All of the fish in the control plot had died from *Cryptocaryon irritans* by the ninth day after exposure. The numbers of *Cryptocaryon irritans* parasites in the left gills of the dead fish were counted, and the average number of *Cryptocaryon irritans* parasites was found to be 20,000 or greater. Cultivating of the fish was continued for 57 days after exposure. No deaths due to *Cryptocaryon irritans* were found for test plot 1 and test plot 2. The numbers of *Cryptocaryon irritans* parasites in the left gills of the remaining fish in Test plot 1 and Test plot 2 were all counted on the 57th day. The average number of parasites was 0.5 for Test plot 1 and 12.7 for Test plot 2. Based on these results, it was determined that there was a *Cryptocaryon irritans* parasite elimination effect even when the amount administered of the combined preparation composed of the inhibitor of folate synthesis and the inhibitor of folate activation was extremely low.

INDUSTRIAL APPLICABILITY

The antiparasitic agent according to the present invention displays the effect of controlling proliferation of fish parasites via oral administration, and shows this effect even against parasites such as ciliate protozoa for which there had not been an effective drug until now. It is possible to use these in the prevention and therapy of parasitosis in cultured fish, etc.

The invention claimed is:

1. A method of killing a fish parasite, comprising administration of 1-50 mg/kg fish body weight/day of an inhibitor of folate synthesis and/or an inhibitor of folate activation to fish infected by a parasite, wherein the parasite belongs to the subkingdom Protozoa Ciliophora.

2. The method according to claim 1, comprising the administration of an inhibitor of folate synthesis and/or an inhibitor of folate activation continuously for 1 to 2 weeks.

3. The method according to claim 1, comprising the administration of the inhibitor of folate synthesis and the inhibitor of folate activation as a combination of drugs.

4. The method according to claim 1, wherein the inhibitor of folate synthesis is a sulfonamide.

5. The method according to claim 4, wherein the sulfonamide is any one of sulfamethoxazole, sulfamonomethoxine, sulfadimethoxine, sulfamerazine, sulfisoxazole, sulfisomidine, sulfamethizole, sulfisozole, or a pharmaceutically acceptable salt thereof.

6. The method according to claim 1, wherein the inhibitor of folate activation is a dihydrofolate reductase inhibitor.

7. The method according to claim 6, wherein the inhibitor of folate activation is any one of pyrimethamine, trimethoprim, ormetoprim, methotrexate, denopterin, pteropterin, aminopterin, edatrexate, piritrexim, or a pharmaceutically acceptable salt thereof.

8. The method according to claim 1, wherein the parasite is *Cryptocaryon irritans* or *Ichthyophthirius multifiliis*.

9. The method according to claim 1, wherein the fish is a *Perciformes, Pleuronectiformes, Clupeiformes, Tetraodontiformes, Cypriniformes, Anguilliformes, Siluriformes, Rajiformes, Characiformes, Labroidei, Anabantoidei, Gobioidei, Cyprinodontiformes, Osteoglossiformes, Semionotiformes, Polypteriformes, Beloniformes, Atheriniformes*, or *Synbranchiformes* fish.

* * * * *